United States Patent
Henchie et al.

(10) Patent No.: US 12,370,067 B2
(45) Date of Patent: Jul. 29, 2025

(54) STENT INCLUDING ANTI-MIGRATION CAPABILITIES

(71) Applicant: BOSTON SCIENTIFIC SCIMED, INC., Maple Grove, MN (US)

(72) Inventors: Travis Henchie, Worcester, MA (US); Shawn Ryan, Littleton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 910 days.

(21) Appl. No.: 17/082,693

(22) Filed: Oct. 28, 2020

(65) Prior Publication Data

US 2021/0121306 A1   Apr. 29, 2021

Related U.S. Application Data

(60) Provisional application No. 62/927,391, filed on Oct. 29, 2019.

(51) Int. Cl.
*A61F 2/82* (2013.01)
*A61F 2/00* (2006.01)

(52) U.S. Cl.
CPC .............. *A61F 2/82* (2013.01); *A61F 2/0077* (2013.01); *A61F 2002/825* (2013.01); *A61F 2210/0076* (2013.01)

(58) Field of Classification Search
None
See application file for complete search history.

(56) References Cited

U.S. PATENT DOCUMENTS

| | | |
|---|---|---|
| 1,836,202 A | 12/1931 | Tiegler |
| 5,876,448 A | 3/1999 | Thompson et al. |
| 6,042,605 A | 3/2000 | Martin et al. |
| 6,099,559 A | 8/2000 | Nolting |
| 6,241,747 B1 | 6/2001 | Ruff |
| 6,258,099 B1 | 7/2001 | Mareiro et al. |
| 6,375,787 B1 | 4/2002 | Lukic |

(Continued)

FOREIGN PATENT DOCUMENTS

| | | |
|---|---|---|
| JP | 2006512099 A | 4/2006 |
| JP | 2011509758 A | 3/2011 |

(Continued)

OTHER PUBLICATIONS

International Search Report and Written Opinion dated Feb. 18, 2021 for International Application No. PCT/US2020/057696.

(Continued)

*Primary Examiner* — Leslie A Lopez
(74) *Attorney, Agent, or Firm* — Seager, Tufte & Wickhem, LLP

(57) ABSTRACT

A medical device for treating a body lumen, such as a medical stent, includes an expandable scaffold configured to shift from a radially collapsed state to a radially expanded state. The stent includes a coating disposed along the outer surface of the expandable scaffold in which a portion of the coating includes a plurality of anti-migration members and one or more preferential separation regions. Each preferential separation region is configured to permit first and second regions of the coating to separate from one another along the preferential separation region therebetween as the expandable scaffold shifts from the radially collapsed state to the radially expanded state.

19 Claims, 19 Drawing Sheets

(56) References Cited

U.S. PATENT DOCUMENTS

| | | |
|---|---|---|
| 6,626,939 B1 | 9/2003 | Burnside et al. |
| 6,676,701 B2 | 1/2004 | Rourke et al. |
| 6,737,160 B1 | 5/2004 | Full et al. |
| 6,759,110 B1 | 7/2004 | Fleming et al. |
| 6,872,439 B2 | 3/2005 | Fearing et al. |
| 6,911,035 B1 | 6/2005 | Blomme |
| 7,056,409 B2 | 6/2006 | Dubrow |
| 7,074,294 B2 | 7/2006 | Dubrow |
| 7,132,161 B2 | 11/2006 | Knowles et al. |
| 7,419,615 B2 | 9/2008 | Strauss |
| 7,691,307 B2 | 4/2010 | Fearing et al. |
| 7,744,914 B2 | 6/2010 | Li et al. |
| 7,763,455 B2 | 7/2010 | Cima et al. |
| 7,828,982 B2 | 11/2010 | Full et al. |
| 7,921,678 B2 | 4/2011 | Norris et al. |
| 8,137,751 B2 | 3/2012 | Bhushan et al. |
| 8,153,254 B2 | 4/2012 | Arzt et al. |
| 8,267,992 B2 | 9/2012 | Atanasoska et al. |
| 8,323,325 B2 | 12/2012 | Valencia |
| 8,365,315 B2 | 2/2013 | Oriz et al. |
| 8,435,286 B2 | 5/2013 | Brister |
| 8,563,117 B2 | 10/2013 | Messersmith et al. |
| 8,703,618 B2 | 4/2014 | Goto et al. |
| 8,716,140 B2 | 5/2014 | Goto et al. |
| 8,720,047 B2 | 5/2014 | Hulseman et al. |
| 8,764,813 B2 | 7/2014 | Jantzen et al. |
| 8,771,354 B2 | 7/2014 | Picha et al. |
| 8,784,473 B2 | 7/2014 | Tupil et al. |
| 8,814,954 B2 | 8/2014 | Hulseman et al. |
| 8,815,385 B2 | 8/2014 | Fearing et al. |
| 8,833,430 B2 | 9/2014 | Aizenberg et al. |
| 8,834,559 B2 | 9/2014 | Mailander et al. |
| 8,874,234 B2 | 10/2014 | Carlsson et al. |
| 8,910,363 B2 | 12/2014 | Palmaz et al. |
| 8,926,688 B2 | 1/2015 | Burkart et al. |
| 8,926,881 B2 | 1/2015 | Ho et al. |
| 9,060,842 B2 | 6/2015 | Karp et al. |
| 9,108,880 B2 | 8/2015 | Jin et al. |
| 9,238,309 B2 | 1/2016 | King et al. |
| 9,242,029 B2 | 1/2016 | Jennissen et al. |
| 9,345,600 B2 | 5/2016 | Jantzen et al. |
| 9,345,601 B2 | 5/2016 | Jantzen et al. |
| 9,486,302 B2 | 11/2016 | Boey et al. |
| 10,130,497 B2 | 11/2018 | Krautkremer et al. |
| 10,195,061 B2 | 2/2019 | Weiner et al. |
| 10,314,726 B2 | 6/2019 | Hollyer et al. |
| 10,441,406 B2 | 10/2019 | Firstenberg et al. |
| 11,298,442 B2 | 4/2022 | Clerc et al. |
| 2002/0010489 A1 | 1/2002 | Grayzel et al. |
| 2002/0082685 A1 | 6/2002 | Sirhan et al. |
| 2002/0123790 A1 | 9/2002 | White et al. |
| 2003/0004535 A1 | 1/2003 | Musbach et al. |
| 2003/0009213 A1 | 1/2003 | Yang |
| 2003/0176911 A1 | 9/2003 | Iancea et al. |
| 2005/0203613 A1 | 9/2005 | Arney et al. |
| 2005/0208100 A1 | 9/2005 | Weber et al. |
| 2005/0255230 A1 | 11/2005 | Clerc et al. |
| 2005/0256564 A1 | 11/2005 | Yang et al. |
| 2005/0271870 A1 | 12/2005 | Jackson |
| 2005/0273121 A1 | 12/2005 | Sato et al. |
| 2006/0069425 A1 | 3/2006 | Hillis et al. |
| 2006/0085062 A1 | 4/2006 | Lee et al. |
| 2006/0136051 A1 | 6/2006 | Furst et al. |
| 2006/0142838 A1 | 6/2006 | Molaei et al. |
| 2006/0193892 A1 | 8/2006 | Furst et al. |
| 2007/0038288 A1 | 2/2007 | Lye et al. |
| 2007/0060998 A1 | 3/2007 | Butterwick et al. |
| 2007/0063375 A1 | 3/2007 | Tuma et al. |
| 2007/0067015 A1 | 3/2007 | Jones et al. |
| 2007/0096048 A1 | 5/2007 | Clerc |
| 2007/0142907 A1 | 6/2007 | Moaddeb et al. |
| 2007/0219619 A1 | 9/2007 | Dieck et al. |
| 2007/0224235 A1 | 9/2007 | Tenney et al. |
| 2007/0276342 A1 | 11/2007 | Lin et al. |
| 2008/0001333 A1 | 1/2008 | Kleine et al. |
| 2008/0077165 A1 | 3/2008 | Murphy |
| 2008/0081271 A1 | 4/2008 | Lee |
| 2008/0086113 A1 | 4/2008 | Tenney et al. |
| 2008/0140182 A1 | 6/2008 | Scheller |
| 2008/0195189 A1 | 8/2008 | Asgari |
| 2008/0199506 A1 | 8/2008 | Horres et al. |
| 2008/0319540 A1 | 12/2008 | Jordan et al. |
| 2009/0041986 A1 | 2/2009 | Zhang et al. |
| 2009/0062927 A1 | 3/2009 | Marten et al. |
| 2009/0069904 A1 | 3/2009 | Picha |
| 2009/0081271 A1 | 3/2009 | Clarke |
| 2009/0088833 A1 | 4/2009 | Soetermans |
| 2009/0130372 A1 | 5/2009 | Fuki et al. |
| 2009/0182303 A1 | 7/2009 | Walak et al. |
| 2009/0187240 A1 | 7/2009 | Clerc et al. |
| 2010/0063579 A1 | 3/2010 | An |
| 2010/0076555 A1 | 3/2010 | Marten et al. |
| 2010/0256064 A1 | 10/2010 | Woolfson et al. |
| 2011/0021965 A1 | 1/2011 | Karp et al. |
| 2011/0172760 A1 | 7/2011 | Anderson |
| 2011/0319980 A1 | 12/2011 | Ryan |
| 2012/0035715 A1 | 2/2012 | Robida et al. |
| 2012/0282391 A1 | 11/2012 | Palmaz et al. |
| 2013/0046371 A1 | 2/2013 | Greenberg et al. |
| 2013/0110255 A1 | 5/2013 | Picha et al. |
| 2013/0184808 A1 | 7/2013 | Hall et al. |
| 2013/0218262 A1 | 8/2013 | Ishii et al. |
| 2013/0231753 A1 | 9/2013 | Liddy et al. |
| 2013/0268063 A1* | 10/2013 | Firstenberg ............... A61F 2/06 623/1.46 |
| 2014/0067046 A1 | 3/2014 | Perry et al. |
| 2014/0148897 A1 | 5/2014 | Matheny |
| 2014/0200679 A1 | 7/2014 | Bluecher et al. |
| 2014/0207251 A1 | 7/2014 | Bluecher et al. |
| 2014/0276203 A1 | 9/2014 | Bertolino et al. |
| 2014/0276407 A1 | 9/2014 | DeVries et al. |
| 2014/0277395 A1 | 9/2014 | Firstenberg et al. |
| 2014/0277442 A1 | 9/2014 | Seddon et al. |
| 2014/0277443 A1 | 9/2014 | Fluery et al. |
| 2014/0277561 A1 | 9/2014 | Jordan |
| 2014/0364959 A1 | 12/2014 | Attar et al. |
| 2015/0051139 A1 | 2/2015 | Chiu et al. |
| 2015/0051693 A1 | 2/2015 | Bertolino |
| 2015/0066136 A1 | 3/2015 | Smith et al. |
| 2015/0282955 A1 | 10/2015 | Guler et al. |
| 2015/0342760 A1* | 12/2015 | Christakis ............... A61F 2/958 623/1.2 |
| 2016/0000553 A1 | 1/2016 | Levi et al. |
| 2016/0120638 A1 | 5/2016 | Michalak |
| 2016/0128852 A1 | 5/2016 | Leanna et al. |
| 2016/0158040 A1 | 6/2016 | Zupkofska et al. |
| 2016/0158513 A1 | 6/2016 | Ryu et al. |
| 2016/0235895 A1 | 8/2016 | Costello |
| 2017/0014111 A1 | 1/2017 | Hulseman et al. |
| 2017/0014247 A1 | 1/2017 | Ryan et al. |
| 2017/0095019 A1 | 4/2017 | Milbocker et al. |
| 2017/0144202 A1 | 5/2017 | King et al. |
| 2018/0043545 A1 | 2/2018 | Hulseman et al. |
| 2018/0043546 A1 | 2/2018 | Hulseman et al. |
| 2018/0100257 A1 | 4/2018 | Hulseman et al. |
| 2018/0168794 A1 | 6/2018 | Bluecher et al. |
| 2019/0076274 A1 | 3/2019 | Hingston et al. |

FOREIGN PATENT DOCUMENTS

| | | |
|---|---|---|
| JP | 2011156083 A | 8/2011 |
| JP | 2012065825 A | 4/2012 |
| JP | 2015504773 A | 2/2015 |
| JP | 2016527051 A | 9/2016 |
| WO | 9951165 A1 | 10/1999 |
| WO | 0101887 A1 | 1/2001 |
| WO | 2010096073 A1 | 8/2010 |
| WO | 2010096072 A1 | 12/2010 |
| WO | 2010138132 A1 | 12/2010 |
| WO | 2013152338 A1 | 10/2013 |

(56) References Cited

FOREIGN PATENT DOCUMENTS

| WO | 2014143750 A1 | 9/2014 |
|---|---|---|
| WO | 2018126238 A1 | 7/2018 |

OTHER PUBLICATIONS

Alfonso et al., "Implications of the 'Watermelon Seeding' Phenomenon During Coronary Interventions for In-Stent Restenosis," Catheterization and Cardiovascular Interventions, 66(4):521-527, Dec. 2005.
Axisa et al., "Low cost, biocompatible elastic and conformable electronic technologies using MID in stretchable polymer," Proceedings of the 29th Annual International Conference of the IEEE, Lyon, France, 2007:6593-6596, Aug. 24-26, 2007.
Conigliaro et al., "Polyflex stents for malignant oesophageal and oesophagogastric stricture: a prospective, multicentric study," European Journal of Gastroenterology & Hepatology, 19(3):195-203, Mar. 2007.
Conio et al., "A Randomized Prospective Comparison of Self-Expandable Plastic Stents and Partially Covered Self-Expandable Metal Stents in the Palliation of Malignant Esophageal Dysphagia," American Journal of Gastroenterology, 102(12):2667-2677, Dec. 2007.
De La Torre et al., "Chronic Wounds," MedScape Reference-Drugs, Diseases and Procedures, WebMD, LLC., New York, NY, updated Dec. 5, 2011 (available online at http://web.archive.org/web/20111210192504/http://emedicine.medscape.com/a-rticle/1298452-overview, last accessed Jul. 3, 2014), 8 pgs.
Desai et al., "Plastic masters-rigid templates for soft lithography," Lab on a Chip, 9(11):1631-1637, 2009.
Dodou et al., "Mucoadhesive micropatterns for enhanced grip," Proceedings of the 29th Annual International Conference of the IEEE, Lyon, France, 2007:1457-1462, Aug. 24-26, 2007.
Jeong et al., "Nanohairs and nanotubes: Efficient structural elements for gecko-inspired artificial dry adhesives," Nano Today, 4(4):335-346, Aug. 2009.
Kroetch, "NanoFab's PDMS Microfluidic Device Fabrication Manual," University of Alberta, Alberta, Canada; 8 pgs, Sep. 2004 (available online at http://www.nanofab.ualberta.ca/wp-content/uploads/2009/03/boxedpdms.pdf, last accessed Mar. 10, 2013).
Kwon et al., "Friction enhancement via micro-patterned wet elastomer adhesives on small intestinal surfaces," Biomedical Materials, 1(4):216-220, Dec. 2006.
Lötters et al., "The mechanical properties of the rubber elastic polymer polydimethylsiloxane for sensor applications," Journal of Micromechanics and Micro engineering, 7(3):145-147, 1997.
Mahdavi et al., "A biodegradable and biocompatible gecko-inspired tissue adhesive," Proceedings of the National Academy of Sciences, U.S.A., 105(7):2307-2312, Feb. 19, 2008.
Majidi, "Enhanced Friction and Adhesion with Biologically Inspired Fiber Arrays," University of California, Berkeley, Ph.D. thesis, 143 pgs, May 15, 2007.
Schembre, "Advances in esophageal stenting: the evolution of fully covered stents for malignant and benign disease," Advanced Therapy, 27(7):413-425, Jul. 2010.
Sharma et al., "Role of esophageal stents in benign and malignant diseases," American Journal of Gastroenterology, 105(2):258-273, Dec. 2009.
Shim, "Esophageal stenting in unusual situations," Endoscopy, 35:14-18, 2003.
Throm Quinlan et al., "Combining dynamic stretch and tunable stiffness to probe cell mechanobiology in vitro," PLoS One, 6(8):e23272, Aug. 2011.
Tooley et al., "Thermal fracture of oxidized polydimethylsiloxane during soft lithography of nanopost arrays," Journal of Micromechanics and Microengineering, 21:054013, Apr. 1-9, 2011.
Van Boeckel et al., "A new partially covered metal stent for palliation of malignant dysphagia: a prospective follow-up study," Gastrointestinal Endoscopy, 72(6):1269-1273, Dec. 2010.
Yoon et al., "Passive control of cell locomotion using micropatterns: the effect of micropattern geometry on the migratory behavior of adherent cells," Lab Chip, 12, 2391-2402 (12 pages), 2012.
Yoon et al., "Passive control of cell locomotion using micropatterns: the effect of micropattern geometry on the migratory behavior of adherent cells," Lab on a Chip, 12(13): Electronic Supplementary Material (ESI) pp. S1-S11, 2012.
PCT International Search Report, PCT International Application No. PCTUS2014/027845 (Filing Date: Mar. 14, 2014), mailed Jul. 15, 2014; 7 pgs.
PCT Written Opinion of the International Searching Authority, PCT International Application No. PCT/US2014/027845 (Filing Date: Mar. 14, 2014), mailed Jul. 15, 2014, 7pgs.
PCT International Search Report, PCT International Application No. PCT/US2013/035531 (Filing Date: Apr. 6, 2013), dated Jul. 1, 2013, 3 pgs.
PCT Written Opinion of the International Searching Authority, PCT International Application No. PCT/US2013/035531 (Filing Date: Apr. 6, 2013) dated Jul. 1, 2013, 5 pgs.
Ara'nzazu Del Campo, et al; "Contact Shape Controls Adhesion of Bioinspired Fibrillar Surfaces," Langmuir, vol. 23, No. 20, pp. 10235-10243, 2007.
PCT International Search Report and Written Opinion, PCT Application No. PCT/US2015/022438 (Filing Date Mar. 25, 2015), dated Jun. 16, 2015, 9 pgs.

* cited by examiner

STENT INCLUDING ANTI-MIGRATION CAPABILITIES

CROSS-REFERENCE TO RELATED APPLICATIONS

This application claims the benefit of priority under 35 U.S.C. § 119 of U.S. Provisional Application No. 62/927,391 filed Oct. 29, 2019, the entire disclosure of which is hereby incorporated by reference.

TECHNICAL FIELD

The present disclosure pertains to medical devices, methods for manufacturing medical devices, and the use thereof. More particularly, the present disclosure pertains to examples of expandable stents having anti-migration capabilities, as well as methods for manufacturing and use thereof.

BACKGROUND

Implantable medical devices (e.g., expandable stents) may be designed to treat strictures in a body lumen and/or provide a fluid pathway for digested material, blood, or other fluid to flow therethrough following a medical procedure. Some medical devices may include radially expandable or self-expanding stents which may be implanted translumically via an endoscope or a stent delivery device, for example. Additionally, some stents may be implanted in a variety of body lumens such as the esophageal tract, the gastrointestinal tract (including the intestine, stomach and the colon), tracheobronchial tract, urinary tract, biliary tract, vascular system, etc.

In some instances it may be desirable to design stents to include sufficient flexibility while maintaining sufficient radial force to open the body lumen at the treatment site. However, in some stents, the compressible and flexible properties that assist in stent delivery may also result in a stent that has a tendency to migrate from its originally deployed position after deployment. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include exposing bare metal portions of the stent to the tissue of the body lumen. The stent scaffold may provide a structure that promotes tissue ingrowth into the interstices or openings thereof. The tissue ingrowth may anchor the stent in place and reduce the risk of stent migration.

Additionally, while it is important to design stents that reduce the degree to which a stent migrates within a body lumen, it also important to design stents that may be easily removed and/or re-positioned from the body lumen post-deployment. Stents including bare portions (i.e., uncovered portions) designed to promote tissue ingrowth (e.g., to reduce stent migration as described above) may also be more difficult to remove once the tissue has anchored the stent in the body lumen. Further, it is also important to design stents that facilitate loading and deploying the stent from a stent delivery device. One method to reduce the stent stiffness and increased radial deployment forces may include reducing the thickness, and hence, the overall volume, of coatings (e.g., anti-migration coatings) applied to the stent. Therefore, in some instances it may be desirable to design a stent having a coating which includes both anti-migration capabilities and a reduced overall volume. Examples of medical devices having coatings which include anti-migration capabilities and reduced volume are disclosed herein.

BRIEF SUMMARY

This disclosure provides design, material, manufacturing method, and use alternatives for medical devices. An example medical stent for treating a body lumen includes an expandable scaffold including a first end region, a second end region opposite the first end region and an outer surface, wherein the expandable scaffold is configured to shift from a radially collapsed state to a radially expanded state. The stent further includes a coating disposed along the outer surface of the expandable scaffold. At least a portion of the coating includes a plurality of anti-migration members. The coating further includes a preferential separation region, the preferential separation region positioned between a first region of the coating and a second region of the coating. Additionally, the preferential separation region is configured to permit the first region of the coating to separate from the second region of the coating along the preferential separation region therebetween as the expandable scaffold shifts from the radially collapsed state to the radially expanded state.

Alternatively or additionally to any of the embodiments above, wherein the preferential separation region is configured to prevent the coating from separating from the outer surface of the expandable scaffold when the expandable scaffold shifts from the radially collapsed state to the radially expanded state.

Alternatively or additionally to any of the embodiments above, wherein the separation of the first region of the coating from the second region of the coating creates an aperture in the coating along the preferential separation region.

Alternatively or additionally to any of the embodiments above, wherein the aperture extends entirely through a wall of the coating.

Alternatively or additionally to any of the embodiments above, wherein the aperture extends through only a portion of a wall of the coating.

Alternatively or additionally to any of the embodiments above, further comprising a plurality of apertures disposed within the coating, wherein the plurality of apertures are aligned along a longitudinal axis of the stent.

Alternatively or additionally to any of the embodiments above, wherein the alignment of the plurality of apertures of the preferential separation regions create a perforated preferential separation region.

Alternatively or additionally to any of the embodiments above, wherein the preferential separation region extends continuously along a longitudinal axis of the stent from the first end region to the second end region.

Alternatively or additionally to any of the embodiments above, wherein the preferential separation region extends linearly along the longitudinal axis of the stent.

Alternatively or additionally to any of the embodiments above, wherein the preferential separation region extends non-linearly along the longitudinal axis of the stent.

Alternatively or additionally to any of the embodiments above, wherein the expandable scaffold includes a plurality of interwoven filaments, and wherein the plurality of filaments are arranged to define a plurality of cells therebetween, and wherein the preferential separation region is positioned within one of the plurality of cells.

Another medical stent for treating a body lumen includes an expandable scaffold including a first end region, a second end region opposite the first end region and an outer surface, wherein the expandable scaffold is configured to shift from a radially collapsed state to a radially expanded state. The stent further includes a coating disposed along the outer surface of the expandable scaffold, wherein at least a portion of the coating includes a plurality of anti-migration members disposed thereon. Additionally, the coating further includes a plurality of preferential separation regions, each of the preferential separation regions spaced apart from one another, and wherein each of the preferential separation regions is configured to define an aperture in the coating when the expandable scaffold shifts from the radially collapsed state to the radially expanded state.

Alternatively or additionally to any of the embodiments above, wherein each of the preferential separation regions is positioned between a first region of the coating and a second region of the coating, and wherein each of the preferential separation regions is configured to permit the first region of the coating to separate from the second region of the coating along each preferential separation region therebetween as the expandable scaffold shifts from the radially collapsed state to the radially expanded state.

Alternatively or additionally to any of the embodiments above, wherein each of the plurality of preferential separation regions is configured to prevent the coating from separating from the outer surface of the expandable scaffold when the expandable scaffold shifts from the radially collapsed state to the radially expanded state.

Alternatively or additionally to any of the embodiments above, wherein the aperture of each of the preferential separation regions extends entirely through a wall of the coating.

Alternatively or additionally to any of the embodiments above, wherein the aperture of each of the preferential separation regions extends through only a portion of the wall of the coating.

Alternatively or additionally to any of the embodiments above, wherein each of the preferential separation regions extends continuously along a longitudinal axis of the stent from the first end region to the second end region.

Alternatively or additionally to any of the embodiments above, wherein each of the preferential separation regions are spaced apart from one another along a longitudinal axis of the stent.

Alternatively or additionally to any of the embodiments above, wherein the expandable scaffold includes a plurality of interwoven filaments, and wherein the plurality of filaments are arranged to define a plurality of cells therebetween, and wherein each of the preferential separation regions is positioned within a corresponding cell of the plurality of cells.

Another medical stent includes an expandable scaffold including a first end region, a second end region opposite the first end region and an outer surface, wherein the expandable scaffold is configured to shift from a radially collapsed state to a radially expanded state. Further, the expandable scaffold includes a plurality of interwoven filaments defining a plurality of cell openings located therebetween. Additionally, the stent includes a coating disposed along the outer surface of the expandable scaffold, wherein at least a portion of the coating includes a micro-pattern, the micro-pattern including a plurality of anti-migration members. Further, the micro-pattern is disposed with the cell openings between the interwoven stent filaments.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
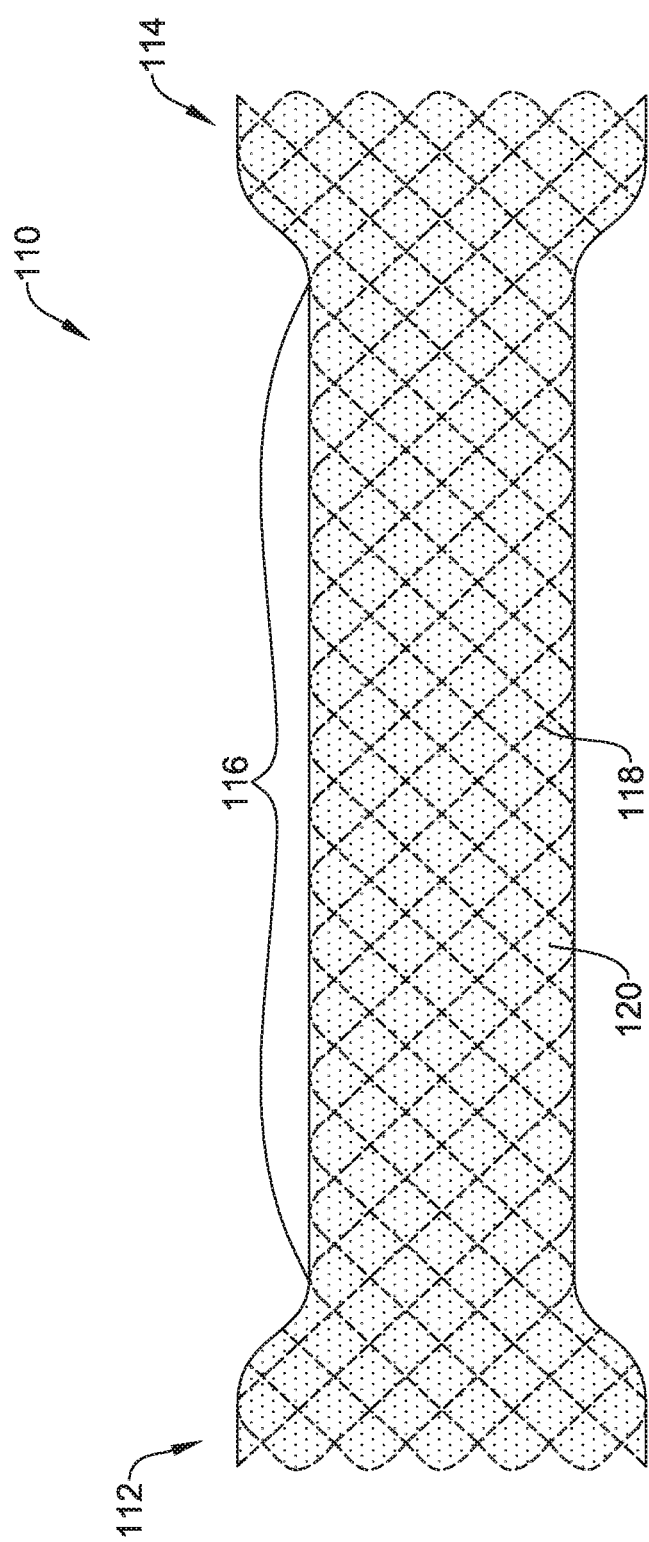
FIG. 1 illustrates an example stent including a covered region.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As discussed above, implantable medical devices may be designed to treat strictures in a body lumen and/or provide a fluid pathway for digested material, or other material or fluid, to flow therethrough following an invasive medical procedure. Examples disclosed herein may include radially or self-expanding stents. The expandable stents may be implanted translumally via an endoscope, or another desired delivery means. Additionally, some stents may be implanted in a variety of body lumens such as the esophageal tract, the gastro-intestinal tract including the intestine and the colon, airways, urinary tracts, biliary tract including bile and/or pancreatic ducts, vascular system, etc.

In some instances, it may be desirable to design stents to include sufficient flexibility to be able to conform to the tortuous body lumen during delivery yet sufficient radial force to open the body lumen at the treatment site. However, in some stents, the compressible and flexible properties that assist in stent delivery may also result in a stent that has a tendency to migrate from its originally deployed position. For example, stents that are designed to be positioned in the esophagus or intestine may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein.

Additionally, while it is important to design stents that reduce the degree to which a stent migrates within a body lumen, it also important to design stents that may be easily removed and/or re-positioned from the body lumen post-deployment. Stents including bare portions (i.e., uncovered portions) designed to promote tissue ingrowth (e.g., to reduce stent migration as described above) may also be more difficult to remove once the tissue has anchored the stent in the body lumen. One method to reduce the force necessary to remove a stent from a body lumen may include covering a portion of the stent, thereby creating a physical barrier between the body lumen and the outer surface of the stent (e.g., reducing the surface area of the stent which may anchored via tissue ingrowth). One method to reduce stent migration while maintaining the ability to remove and/or reposition the stent may include designing the outer surface of the stent to include an anti-migration surface texture. For example, a stent scaffold may include a gripping structure (e.g., a micro-pattern gripping structure) that improves the surface friction of the stent. The increased surface friction may anchor the stent in place and reduce the risk of stent migration. Example medical devices including a micro-pattern surface texture are disclosed below.

FIG. 1 illustrates an example implantable medical device, illustrated as a stent 110. However, although illustrated as a stent, the implantable medical device 110 may be any of a number of devices that may be introduced endoscopically, subcutaneously, percutaneously or surgically to be positioned within an organ, tissue, or lumen, such as an esophagus, intestine, colon, urethra, trachea, bronchus, bile duct, blood vessel, or the like. The stent 110 may be configured to be positioned in a body lumen for a variety of medical applications. For example, the stent 110 may be used to treat a stricture in a body lumen. Additionally, the stent 110 may be used to provide a pathway for food or other digested materials to pass therethrough without directly contacting adjacent tissue. It is contemplated that the examples described herein may be utilized in the esophageal tract, as well as in the gastrointestinal, vascular, urinary, biliary, tracheobronchial, or renal tracts, for example. In some instances, the stent 110 (e.g., an intestinal stent, an esophageal stent, a vascular stent, tracheal stent, bronchial stent, etc.) may include an expandable scaffold.

The expandable scaffold of the stent 110 may have a first end region 112 and a second end region 114 positioned on an opposite end of the stent 110 from the first end region 112. In some instances, the first end region 112 may extend to a first end of the stent 110 and the second end region 114 may extend to a second end of the stent 110 opposite the first end. The expandable scaffold of the stent may include a medial region 116 extending between the first end region 112 and the second end region 114, or otherwise positioned between the first and second end regions 112, 114 of the implantable medical device 110 to form an expandable tubular framework or scaffold with open ends and defining a lumen extending therethrough. As shown in FIG. 1, the first end region 112 and/or the second end region 114 may include a flared portion having an enlarged outer diameter greater than the outer diameter of the medial region 116 in a radially expanded configuration, if desired. For example, FIG. 1 illustrates both the first end region 112 and the second end region 114 having an outer diameter that is greater than the outer diameter of the medial region 116 in the radially expanded configuration. In other embodiments, only one of the first end region 112 and the second end region 114 may include a flared portion, or the expandable scaffold of the stent 110 may have a constant outer diameter along its entire length, if desired.

A plurality of strut members 118 may be arranged in a variety of different designs and/or geometric patterns to form the expandable tubular framework or scaffold of the stent 110. Numerous designs, patterns and/or configurations for the stent cell openings (e.g., the openings between adjacent strut members), strut thicknesses, strut designs, stent cell shapes are contemplated and may be utilized with embodiments disclosed herein. Further, self-expanding stent examples disclosed herein may include stents having one or more strut members 118 combined to form a rigid and/or semi-rigid stent structure. In some examples disclosed herein, the collection of strut members 118 forming a rigid and/or semi-rigid framework structure may be referred to as a scaffold. For example, the strut members 118 may be wires or filaments that are braided, intertwined, interwoven, weaved, knitted, crocheted or the like to form the expandable scaffold or framework of the stent 110. The strut members (e.g., wires or filaments) 118 of the stent 110 may be configured to self-expand to an expanded diameter when unconstrained. Alternatively, the strut members 118 may be formed from a monolithic structure (e.g., a cylindrical tubular member), such as a single, cylindrical tubular laser-cut Nitinol tubular member, in which the remaining portions of the tubular member form the strut members 118. The monolithic structure of the stent 110 may be configured to self-expand to an expanded diameter when unconstrained.

The expandable scaffold of stent 110 in at least some examples disclosed herein may be constructed from a variety of materials. For example, the expandable scaffold of the stent 110 may be constructed from a metal (e.g., Nitinol). In other instances, the expandable scaffold of the stent 110 may be constructed from a polymeric material (e.g., PET). In yet other instances, the expandable scaffold of stent 110 may be constructed from a combination of metallic and polymeric materials. Additionally, the expandable scaffold of stent 110 or portions thereof may include a bioabsorbable and/or biodegradable material.

As discussed above, in some instances the stent 110 may include a coating 120 (indicated by the dotted pattern in FIG. 1) disposed along the expandable scaffold 118 of the stent 110. In some examples, the coating 120 may be referred to as a first coating layer or a base coating layer. The base coating layer 120 may be applied to the expandable scaffold prior to the application of additional coating layers (as will be described below). While FIG. 1 illustrates the coating 120 extending along the entire length and circumference of the stent 110, in some examples, the coating 120 may be disposed along only a portion of the stent 110. Further, the coating 120 may fully cover the stent 110, thus extending across or spanning the interstices (e.g. cell openings) between struts 118 of the expandable framework or scaffold of the stent 110. In other words, the coating 120 may entirely surround the expandable framework or scaffold of the stent 110 to fully enclose the interstices of the expandable framework, and thus prevent tissue ingrowth into the lumen of the stent 110. While FIG. 1 shows the coating 120 extending along the outer surface of strut members 118, it is contemplated that coating 120 may extend along the inner surface of strut members 118 and/or may fully surround or encapsulate the strut members 118. Additionally, as will be discussed in greater detail below, the coating 120 may be applied by spraying, dipping, spinning or attaching a polymer sheet or tube to the inner and/or outer surface of the stent filaments 18.

In some instances, the coating 120 may include an elastomeric or non-elastomeric material. Further, a portion of the coating 120 may be formed from a suitable material, such as a biostable material. For example, the coating 120 may include a polymeric material, such as silicone, polytetrafluoroethylene, polyurethane, or the like, or other materials including those disclosed herein. Further, a portion of the coating 120 may be a biostable material. For purposes of discussion herein, a biostable material may be defined as a material that does not biodegrade. For example, the coating 120 may include a polymeric material, such as silicone, polytetrafluoroethylene, polyurethane, or the like, or other materials including those disclosed herein. In other examples, the coating 120 may be constructed from fabric, PEEK, ABS, PLS or other suitable materials. Additionally, the coating 120 may include 3D printed materials.

Figure 2:
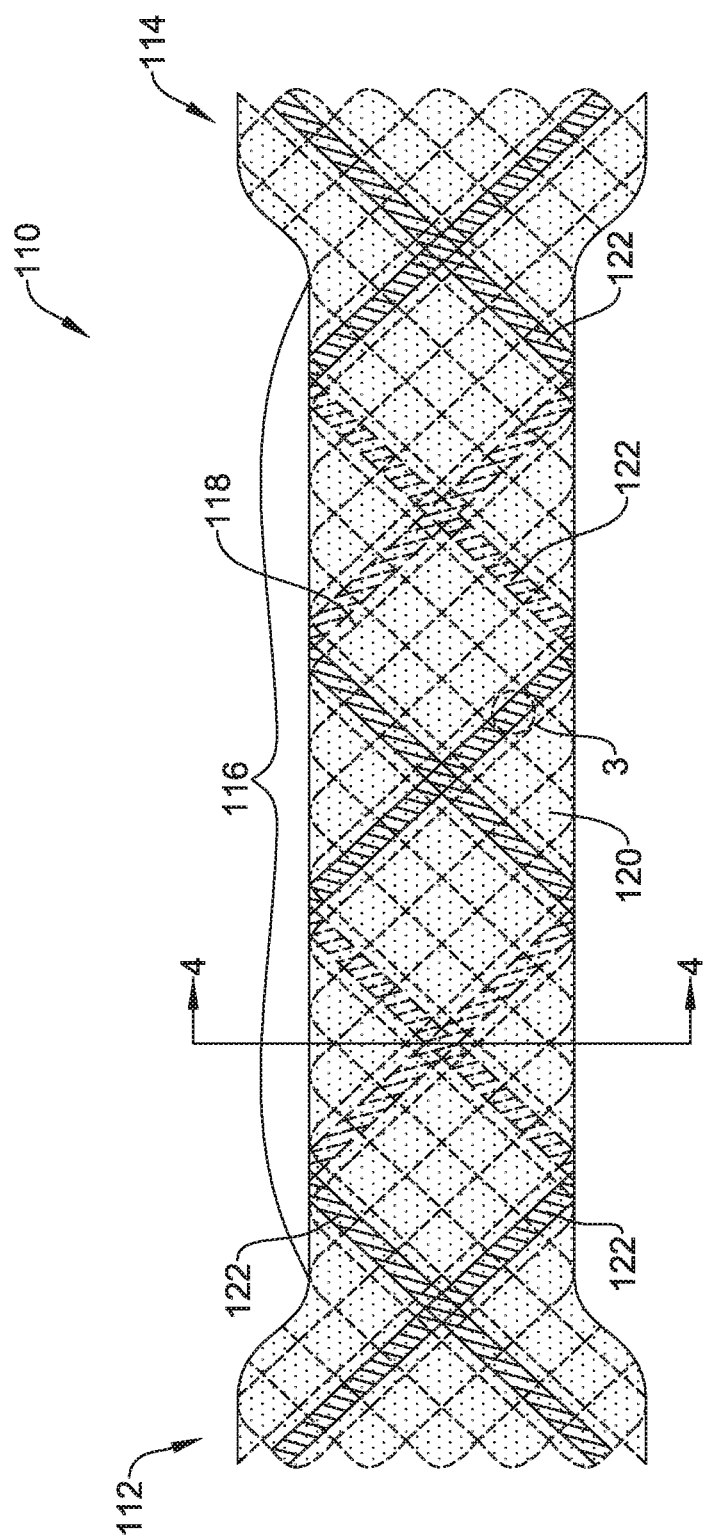
FIG. 2 illustrates another example stent including a covered region and a micro-pattern.

As discussed above, in some examples, it may be desirable to design the stent 110 to include one or more features which increase the surface friction of the stent 110. For example, FIG. 2 illustrates that, in some examples, the coating of the stent 110 may in addition to the base coating layer 120 or alternative to the base coating layer 120 include a micro-pattern coating layer 122 formed from a plurality of anti-migration elements. A detailed discussion of the individual anti-migration elements which, collectively, form the micro-pattern coating layer 122 will be discussed in greater detail below with respect to FIG. 3. The micro-pattern coating layer 122 may be designed to reduce stent migration while maintaining the ability to remove and/or reposition the stent 110. As discussed above, and as will be described in greater detail below, the anti-migration elements forming the micro-pattern coating layer 122 may include a plurality of gripping structures (e.g., a micro-pattern gripping structures) that improves the surface friction of the stent 110.

Further, FIG. 2 illustrates that the micro-pattern coating layer 122 may be arranged along only select portions of the expandable scaffold of the stent 110 in a variety of arrangements, without being applied to the entire length and/or circumference of the expandable scaffold of the stent 110. For example, FIG. 2 illustrates the micro-pattern coating layer 122 arranged around the stent 110 in a helical arrangement. In other words, the micro-pattern coating layer 122 is arranged in one or more, or a plurality of helical strips extending helically around the outer surface of the stent 110.

FIG. 2 shows that the helical micro-pattern 122 extending along the stent 110 includes a pitch angle. However, it can be appreciated that, in other examples, the pitch angle of the micro-pattern coating layer 122 (forming the one or more helical strips) may vary. In other words, other example stent designs may include a micro-pattern coating layer 122 which is arranged in a helix having a greater or lesser pitch angle than the pitch angle illustrated in FIG. 2.

Additionally, FIG. 2 illustrates the micro-pattern coating layer 122 extending from the first end region 112 (including along the flared portion of the stent 110) to the second end region 114 of the stent 110 (including along the flared portion of the stent 110). However, it is contemplated that the micro-pattern coating layer 122 may extend along any portion of the stent 110. For example, the micro-pattern coating layer 122 may disposed along only the medial region 116. In other examples, the micro-pattern coating layer 122 may be disposed along both the medial region 116 and one or more of the first end region 112 and/or the second end region 114 of the stent 110.

Figure 3:
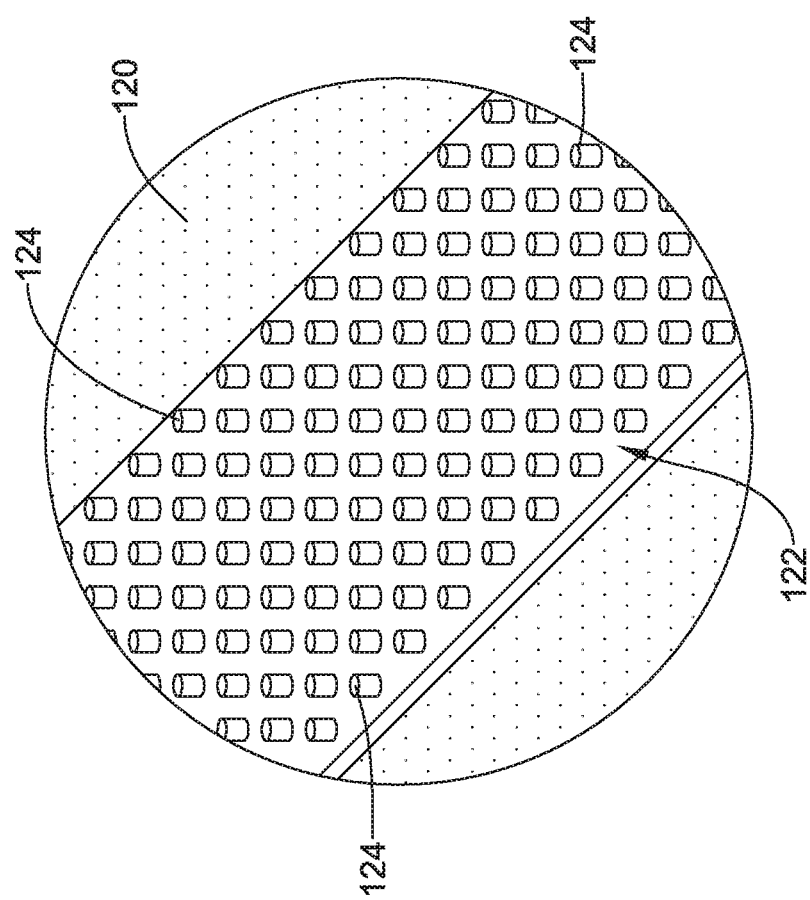
FIG. 3 illustrates a detailed view of a portion of the stent shown in FIG. 2.

FIG. 3 illustrates the detailed view of FIG. 2. FIG. 3 illustrates that the micro-pattern coating layer 122 shown in FIG. 2 may be formed from a collection (e.g., a plurality) of individual anti-migration elements 124 extending from a base of the micro-pattern coating layer 122. Each of the anti-migration elements 124 may be spaced relatively close to one another, thereby, collectively, forming a surface texture or gripping surface which reduces the potential for the stent 110 to migrate when deployed in a body lumen.

FIG. 3 further illustrates that each individual anti-migration element 124 may be shaped as a cylinder (e.g., pillar).

However, it is contemplated that the individual anti-migration elements 124 may include a variety of shapes. For example, each anti-migration element 124 may be rounded, square, triangular, ovular, polygonal, diamond-shaped, pillars, rectangular, spikes, hooks, any suitable geometric shape or combinations thereof. Example shapes of other anti-migration elements 124 are disclosed in U.S. Patent Publication No. US2013/0268063, the entirety of which is herein incorporated by reference.

In some examples, the micro-pattern coating layer 122 (including the anti-migration elements 124) may be formed by first depositing the material utilized for the micro-pattern coating layer 122 onto the base coating layer 120, followed by stamping the micro-pattern coating layer 122 to form the individual anti-migration elements 124 (e.g., stamping a portion of the micro-pattern coating layer 122 to form each of the anti-migration elements 124 which collectively form the micro-pattern coating layer 122). In some examples, the micro-pattern coating layer 122 may include a liquid silicone that is applied to the base coating 120. For example, the liquid silicone may be layered onto a mold which has the micro-pattern inlayed thereon. After allowing that layer of silicone to cure, it may be attached to the base coating 120 via an additional layer of liquid silicone (e.g., a layer of liquid silicone may be utilized to attach the molded micro-pattern silicone to the base coating 120). In other embodiments, however, the micro-pattern coating layer may be molded directly onto the base coating layer 120, or molded and subsequently applied to the base coating layer 120.

Additionally, it can be appreciated that, in other examples, the anti-migration elements 124 shown in FIG. 3 may be formed by stamping the base coating layer 120. For example, in some instances, the anti-migration elements 124 may be formed by stamping a portion of the base coating layer 120 to form each of the anti-migration elements 124).

In yet other examples, the micro-pattern coating layer 122 (including the anti-migration elements 124) may be formed along the stent 110 by positioning a sleeve (e.g., sheath, tube, etc.) along the filaments 118 of the stent 110. It can be appreciated that the sleeve may have been formed to include the micro-pattern coating layer 122 prior to being positioned and affixed to the stent 110. For example, a sleeve including the micro-pattern coating layer 122 illustrated in FIG. 3 may be formed in a first manufacturing step, such as by molding, whereby the sleeve is then coupled to the outer surface of the stent 110 in a second manufacturing step.

Figure 4:
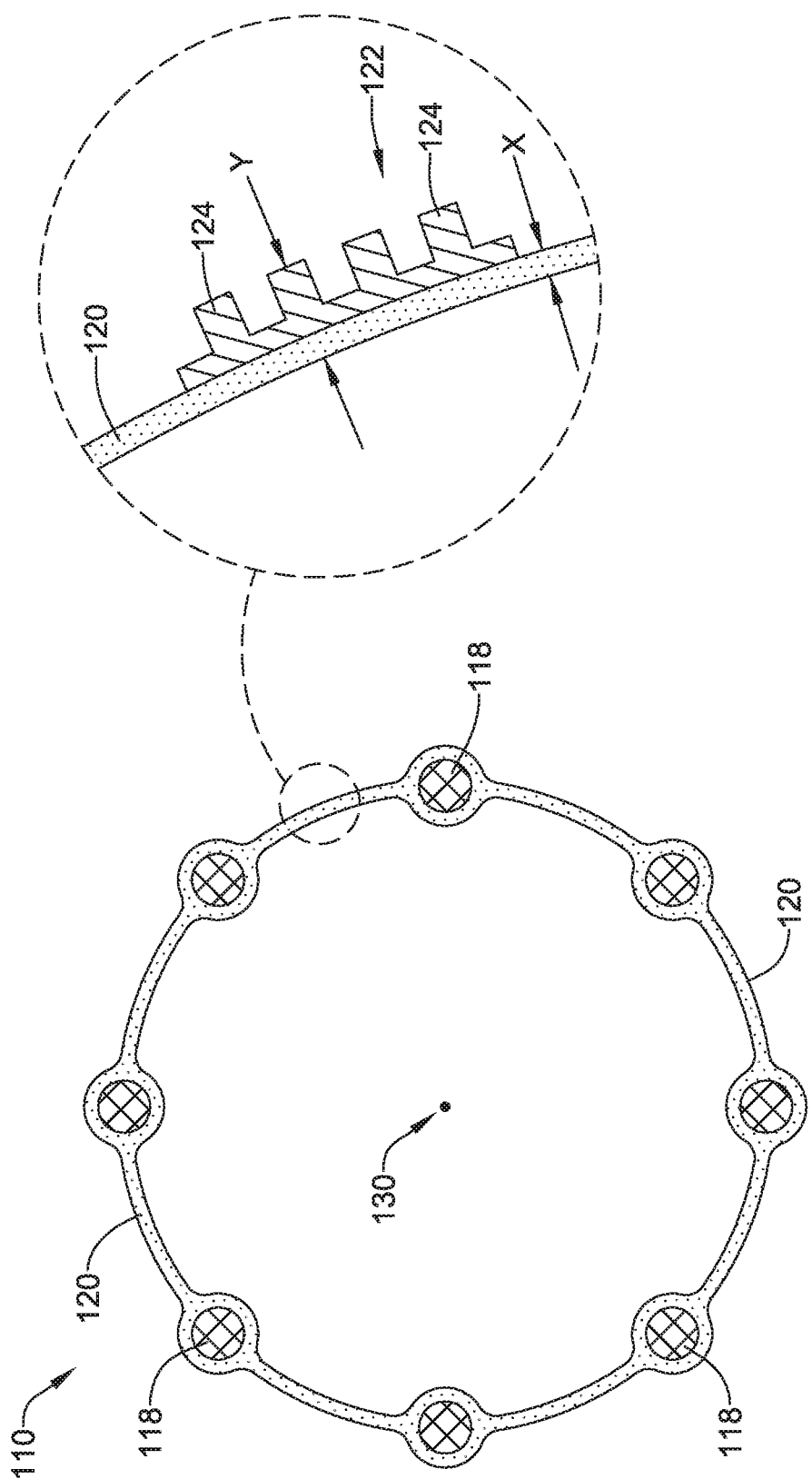
FIG. 4 illustrates a cross-sectional view along line 4-4 of the stent shown in FIG. 2.

FIG. 4 illustrates a cross-section taken along line 4-4 of FIG. 3. FIG. 4 shows the stent filaments 118 arranged around a central longitudinal axis 130 of the stent 110. Further, FIG. 4 illustrates the base coating layer 120 surrounding each of the individual filaments 118. Additionally, FIG. 4 illustrates that the base coating layer 120 may span across the cell openings of the stent 110.

Additionally, the detailed view of FIG. 4 illustrates a cross-sectional view of the base coating layer 120, the micro-pattern coating layer 122 and a plurality of the anti-migration members 124 described above. As shown in the detailed view of FIG. 4, the base coating layer 120 may have a thickness "X." In some examples, the thickness of the base coating layer 120 may be about 20-80 microns, or may be about 30-70 microns, or may be about 40-60 microns, or may be about 40-70 microns, or may be about 30-80 microns, or about 50 microns. Additionally, the detailed view of FIG. 4 illustrates that the entire thickness of the coating on the stent scaffolding, including the base coating layer 120 and the micro-pattern coating layer 122) may have a thickness "Y." In some examples, the entire thickness of the coating on the stent scaffolding (including the combined thickness of the base coating 120 and the thickness of the micro-pattern coating layer 122 to the tip of the anti-migration members 124) may be about 40-220 microns, or may be about 80-180 microns, or may be about 60-200 microns, or may be about 80-170 microns, or may be about 100-170 microns, or may be about 90-150 microns, or may be about 100-140 microns, or may be about 110-130 microns, or about 120 microns.

It can be appreciated that the portions of the micro-pattern coating 122 which are thicker (versus other, thinner portions of the base coating layer 120) may form an outwardly-extending surface texture or gripping surface which reduces the potential for the stent 110 to migrate when deployed in a body lumen, while the reduced thickness of the base coating layer 120 of the coating may permit the stent 110 to radially collapse and/or radially expand with less resistance. It can be appreciated from the above discussion that the addition of a micro-pattern coating layer (e.g., the micro-pattern coating layer 122) to the outer surface of an example stent will increase the overall coating volume of the stent. It can be further appreciated that, in some examples, this additional coating volume may increase the axial stiffness and/or radial deployment forces of the stent (e.g., the stent 110). Therefore, it can be further appreciated that the application of a micro-pattern coating layer (e.g., the layer 122) along only portions of the outer surface of the stent may reduce (e.g., mitigate) the undesirable effects associated with having a micro-pattern coating layer disposed along the entire outer surface of the stent. In other words, it may be desirable to reduce the overall volume of the stent (and thereby improve stent stiffness and radial deployment forces) by applying the micro-pattern coating layer (e.g., layer 122) along only select portions of the stent. Additionally, reducing the overall coating thickness of the stent may provide additional advantages when trying to load the stent into a delivery device. For example, limiting the coating in various locations may not only lower the overall volume of the coating but it may also aid in maintaining the mechanical properties of the stent where the foreshortening and radial forces are not greatly compromised, thereby permitting the stent to compress to a greater reduced diameter and facilitate easier stent loading into a stent delivery device.

Further, FIG. 4 illustrates the anti-migration elements 124 may be disposed along the stent 110 such that the anti-migration elements 124 extend radially away of the strut members 118 of the expandable scaffold. As discussed above, base coating layer 120 and/or the micro-pattern coating layer 122 may extend across the interstices or openings between adjacent struts 118. Further, FIG. 4 illustrates that the micro-pattern coating layer 122 may be positioned at an outermost surface of the stent 110 such that it contacts the inner surface of a body lumen in which the stent 110 may be deployed.

As shown in FIG. 4, it can be appreciated that the micro-pattern coating layer 122 may form a textured and/or a roughened surface designed to contact and engage with the inner surface of an example body lumen engaged therewith. For example, in some instances, the textured micro-pattern coating layer 122 surface may temporarily anchor the covered portion of stent 110 along the inner surface of an example body lumen.

Figure 5:
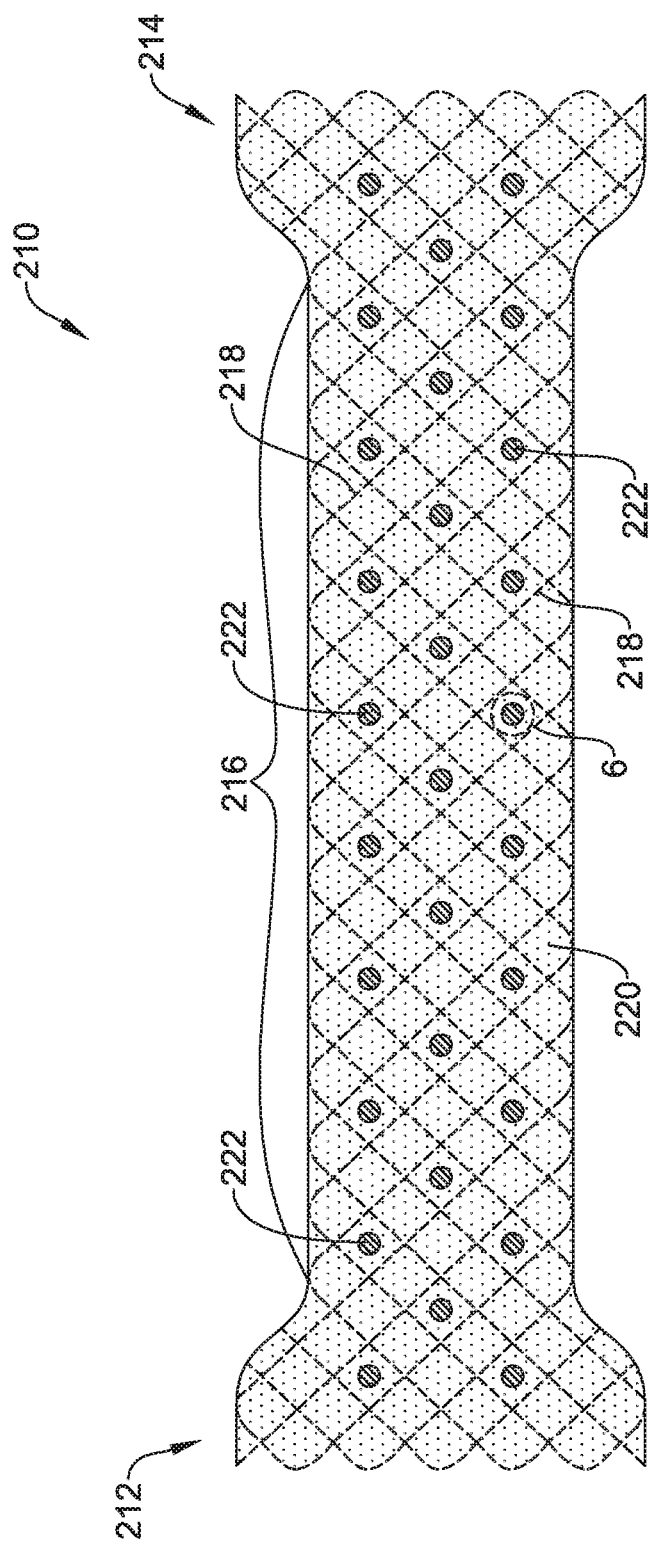
FIG. 5 illustrates another example stent including a covered region and a micro-pattern.

FIG. 5 illustrates another example stent 210. The stent 210 may be similar in form and function to the stent 110 described above. For example, the stent 210 may include an expandable scaffold (including one or more interwoven filaments 218 arranged to form the expandable scaffold)

extending from a first end region 212 to a second end region 214. A medial region 216 may extend between the first end region 212 and the second end region 214. The first end region 212 and/or the second end region 214 may include a flared portion having an enlarged outer diameter greater than the outer diameter of the medial region 216 in a radially expanded configuration, if desired. Additionally, the stent 210 may include a base coating layer 220 disposed along the expandable scaffold of the stent 210.

FIG. 5 further illustrates that a portion of the stent 210 may include a distinct micro-pattern coating layer 222 formed from a plurality of anti-migration elements, similar to that described above. However, the micro-pattern coating layer 222 illustrated in FIG. 5 may be arranged in a "dot" pattern. In other words, the micro-pattern coating layer 222 may include a plurality of individual discontinuous areas of the coating (e.g., discontinuous patches) that are spaced apart from other discontinuous individual areas of the coating (e.g., other discontinuous patches) of the micro-pattern coating layer 222, with each discontinuous area of the micro-pattern coating layer 222 including a plurality of anti-migration elements formed thereon. The discontinuous patches of the micro-pattern coating layer 222 may be disposed along the length and/or circumference (or any portion) of the stent 210. Each area/patch (e.g., region, portion, etc.) of anti-migration elements may be separate and spaced apart from one another. Further, each area/patch of anti-migration elements may be arranged in a desired shape, such as a circular shape (e.g., dots), if desired. The sum of all the discontinuous areas of anti-migration elements may be referred to as the micro-pattern coating layer 222, as shown in FIG. 5.

In some examples, one or more of the micro-pattern coating layer 222 "dots" may be aligned with one another along the entire length (or a portion thereof) of the stent 210. However, in other examples, the micro-pattern coating layer 222 dots may not be aligned with one another. Rather, the micro-pattern coating layer 222 dots may be arranged in a variety of patterns along the stent 210. In some examples, the micro-pattern coating layer 222 dots may be arranged in a random distribution.

Additionally, FIG. 5 illustrates the micro-pattern coating layer 222 extending from the first end region 212 (including along the flared portion of the stent 210) to the second end region 214 (including along the flared portion of the stent 210). However, it is contemplated that the micro-pattern coating layer 222 may extend along any portion of the stent 210. For example, the micro-pattern coating layer 222 may only be positioned along the medial region 216 or along the medial region 216 and one or more of the first end region 212 and/or the second end region 214 of the stent 210.

Figure 6:
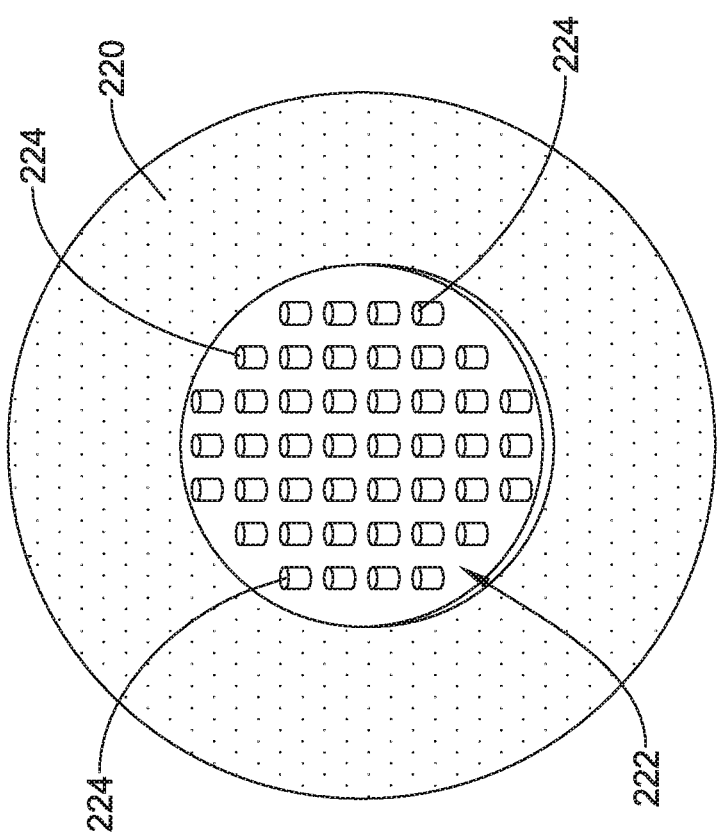
FIG. 6 illustrates a detailed view of a portion of the stent shown in FIG. 5.

FIG. 6 illustrates the detailed view shown in FIG. 5. Like FIG. 3, FIG. 6 illustrates that the micro-pattern coating layer 222 shown in FIG. 3 may include an array (e.g., a plurality) of individual anti-migration elements 224 extending radially outward from a base portion of the micro-pattern coating layer 222. Each of the anti-migration elements 224 may be spaced relatively close to one another, thereby, collectively, forming a surface texture or gripping surface which reduces the potential for the stent 210 to migrate when deployed in a body lumen.

Additionally, FIG. 6 illustrates that the plurality of anti-migration elements 224 may be arranged to collectively form a circle (e.g., one "dot" of the dot micro-pattern coating layer 222 described above). It is contemplated that the anti-migration elements 224 may be formed similarly to other micro-pattern structures described herein. For example, the micro-pattern coating layer 222 shown in FIG. 6 may be formed by applying the material utilized to form the micro-pattern coating layer 222 onto the base coating layer 220, followed by stamping the micro-pattern coating layer 222 into the individually-shaped anti-migration elements 224. Alternatively, the micro-pattern coating layer 222 may be molded separately, and subsequently applied to the base coating layer 220. Additionally, the micro-pattern coating layer 222 illustrated in FIG. 6 may be disposed along any portion of the stent 210.

Figure 7:
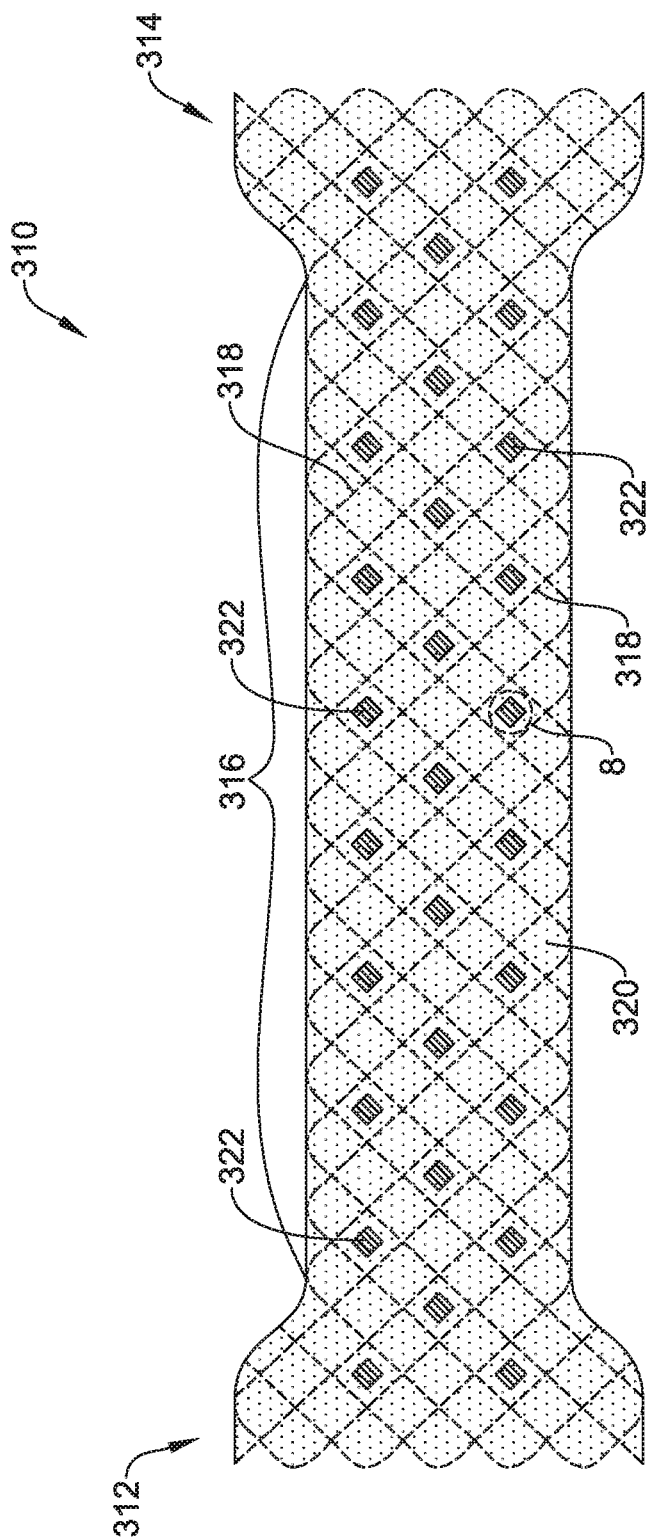
FIG. 7 illustrates another example stent including a covered region and a micro-pattern.

FIG. 7 illustrates another example stent 310. The stent 310 may be similar in form and function to other example stents described above. For example, the stent 310 may include an expandable scaffold (including one or more interwoven filaments 318 arranged to form the expandable scaffold) extending from a first end region 312 to a second end region 314. A medial region 316 may extend between the first end region 312 and the second end region 314. The first end region 312 and/or the second end region 314 may include a flared portion having an enlarged outer diameter greater than the outer diameter of the medial region 316 in a radially expanded configuration, if desired. Additionally, the stent 310 may include a base coating layer 320 disposed along the expandable scaffold of the stent 310.

FIG. 7 further illustrates that a portion of the stent 310 may include a distinct micro-pattern coating layer 322 formed from a plurality of anti-migration elements, similar to that described above. However, the micro-pattern coating layer 322 illustrated in FIG. 7 may include a plurality of individual "diamond" patterns. In other words, the micro-pattern coating layer 322 may include a plurality of individual discontinuous areas of the coating (e.g., discontinuous patches) that are spaced apart from other discontinuous individual areas of the coating (e.g., other discontinuous patches) of the micro-pattern coating layer 322, with each discontinuous area of the micro-pattern coating layer 322 including a plurality of anti-migration elements formed thereon. The discontinuous patches of the micro-pattern coating layer 322 may be disposed along the length and/or circumference (or any portion) of the stent 310. Each area/patch (e.g., region, portion, etc.) of anti-migration elements may be separate and spaced apart from one another. Further, each area/patch of anti-migration elements may be arranged in a desired shape, such as a diamond shape, if desired. The sum of all the discontinuous areas of anti-migration elements may be referred to as the micro-pattern coating layer 322, as shown in FIG. 7.

In some examples, one or more of the micro-pattern coating layer 322 "diamonds" may be aligned with one another along the entire length (or a portion thereof) of the stent 310. However, in other examples, the micro-pattern coating layer 322 diamonds may not be aligned with one another. Rather, the micro-pattern coating layer 322 diamonds may be arranged in a variety of patterns along the stent 310. In some examples, the micro-pattern coating layer 322 diamonds may be arranged in a random distribution.

Additionally, FIG. 7 illustrates the micro-pattern coating layer 322 extending from the first end region 312 (including along the flared portion of the stent 310) to the second end region 314 (including along the flared portion of the stent 310). However, it is contemplated that the micro-pattern coating layer 322 may extend along any portion of the stent 310. For example, the micro-pattern coating layer 322 may only be positioned along the medial region 316 or along the medial region 316 and one or more of the first end region 312 and/or the second end region 314 of the stent 310.

Figure 8:
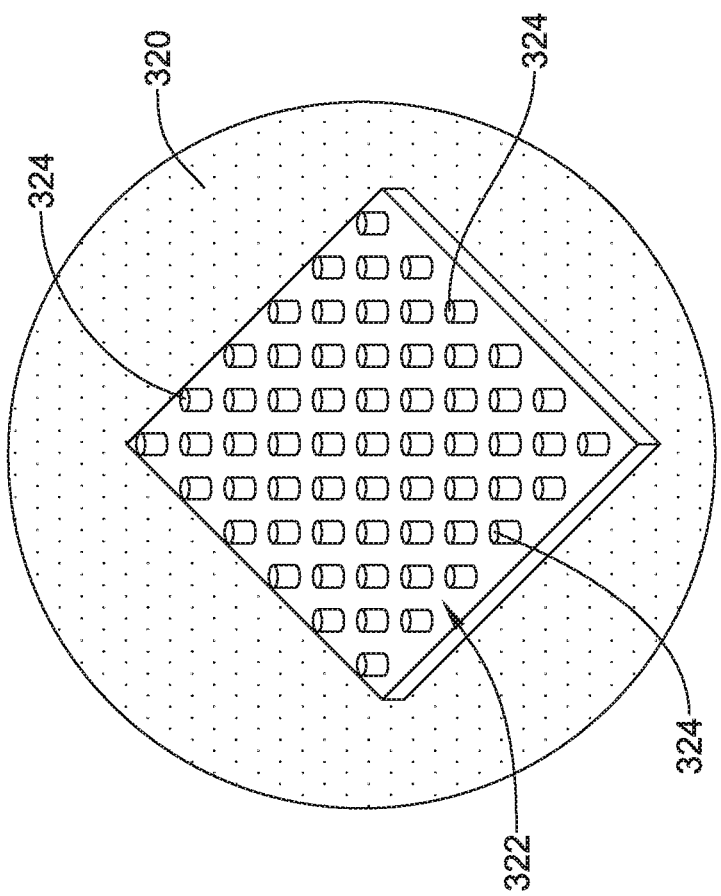
FIG. 8 illustrates a detailed view of a portion of the stent shown in FIG. 7.

FIG. 8 illustrates the detailed view shown in FIG. 7. FIG. 8 illustrates that the micro-pattern coating layer 322 shown in FIG. 7 may be formed from an array (e.g., a plurality) of individual anti-migration elements 324. Each of the anti-migration elements 324 may be spaced relatively close to one another, thereby, collectively, forming a surface texture or gripping surface which reduces the potential for the stent 310 to migrate when deployed in a body lumen.

Additionally, FIG. 8 illustrates that the plurality of anti-migration elements 324 may be arranged to collectively form a diamond shape (e.g., one "diamond" of the micro-pattern 322 described above). It is contemplated that the anti-migration elements 324 may be formed similarly to other micro-patterns described herein. For example, the micro-pattern coating layer 322 shown in FIG. 8 may be formed applying the material utilized to form the micro-pattern coating layer 322 onto the base coating layer 320, followed by stamping the micro-pattern coating layer 322 into the individually-shaped anti-migration elements 324. Alternatively, the micro-pattern coating layer 322 may be molded separately, and subsequently applied to the base coating layer 320. Additionally, the micro-pattern coating layer 322 illustrated in FIG. 8 may be disposed along any portion of the stent 310.

In some examples (such as the example micro-pattern described with respect to FIGS. 7 and 8), one or more of the individual diamond patches which collectively form the micro-pattern coating layer 322 may be positioned in-between adjacent filaments 318 of the stent 310. In other words, the micro-pattern coating layer 322 may be formed such that the individual anti-migration elements 324 are located in the area entirely between the stent struts 318, thus reducing the overall radial thickness of the stent 310 in the areas having the micro-pattern coating layer 322.

While the above examples described with respect to FIGS. 2-8 illustrate several different micro-pattern coating layer arrangements, it can be appreciated that that a variety of different micro-pattern coating layer arrangements may be contemplated. For example, the micro-pattern coating layer may include stripes extending along the longitudinal axis of the stent and/or bands which extend circumferentially around the outer surface of the stent. In other examples, the micro-pattern coating layer may include chevron-like patterns oriented to reduce stent migration or the micro-pattern coating may be applied on only the flared portions, medial regions or the distal portions. Additionally, the micro-pattern coating layer may include a combination of dots, squares, stripes, helix, etc.

Figure 9:
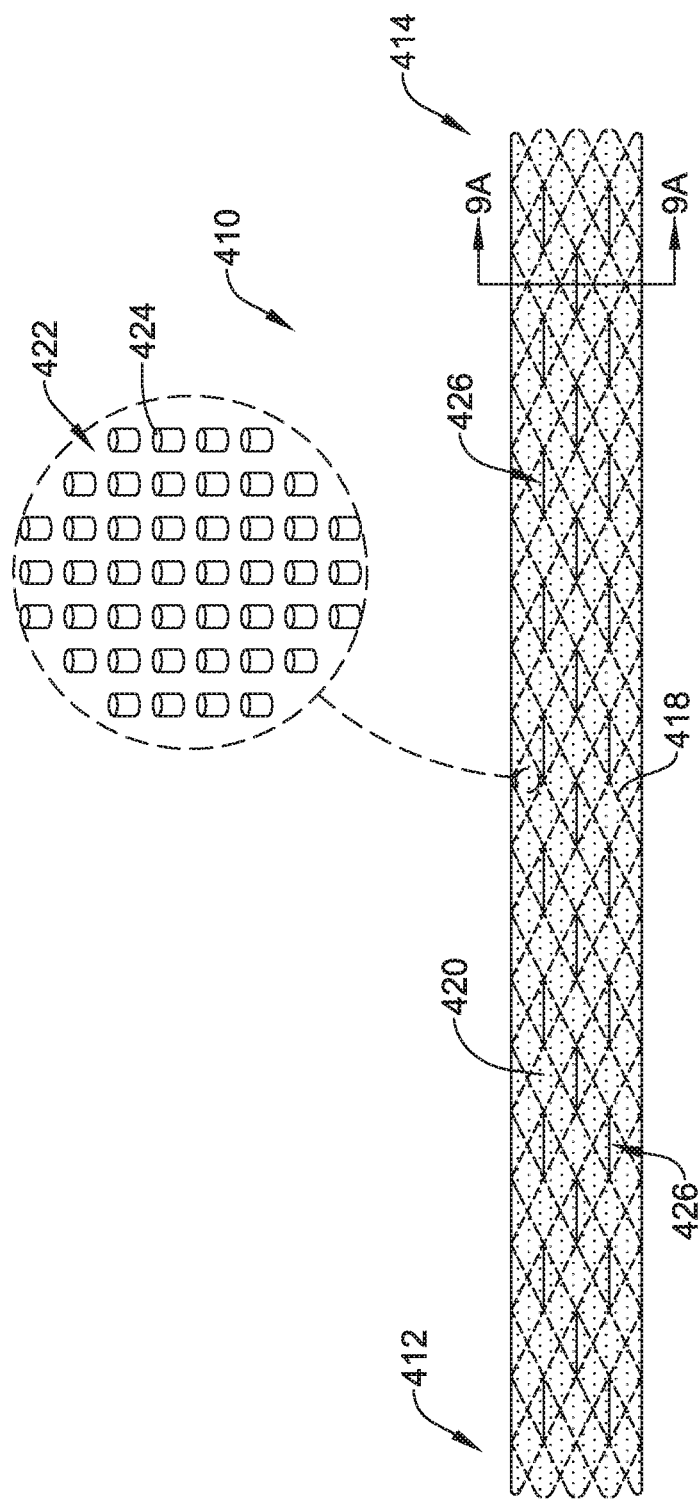
FIG. 9 illustrates another example stent in a pre-deployed configuration having a covered region and a micro-pattern.

FIG. 9 illustrates another example stent 410. The stent 410 may be similar in form and function to other example stents described above. For example, the stent 410 may include an expandable scaffold (including one or more interwoven filaments 418 arranged to form the expandable scaffold) extending from a first end region 412 to a second end region 414. Further, the stent 410 may include a base coating 420 disposed along the expandable scaffold of the stent 410. Further yet, the stent 410 may include a micro-pattern coating layer 422 disposed along the base coating 420, whereby the micro-pattern coating layer 422 extends along the entire length and around the entire circumference of the stent 410. The micro-pattern coating layer 422 may be similar in form and function to other micro-pattern coating layer disclosed herein. For example, as shown in the detailed view of FIG. 9, the micro-pattern coating layer 422 may include a plurality of anti-migration elements 424 extending radially outward from a base portion of the micro-pattern coating layer 422. The anti-migration elements 424 may be designed to provide an additional gripping force to the exterior surface of the stent 410.

Additionally, FIG. 9 illustrates the stent 410 in an unexpanded (e.g., pre-deployed) configuration. In other words, the stent 410 shown in FIG. 9 has a reduced outer diameter as compared to the stent 410 in a deployed configuration (shown in FIG. 10). Further, in some instances it may be desirable to design the stent 410 to include one or more "preferential separation regions" 426. In the stent example shown in FIG. 9, the individually-spaced separation regions 426 may extend longitudinally along the stent 410. For example, the micro-pattern coating layer 422 may include a plurality of discontinuous preferential separation regions 426 arranged at desired intervals along the length and circumference of the stent 410.

It can be appreciated that the preferential separation regions 426 may include strategically placed apertures, notches, slits, slots, channels, grooves, voids, or stress raisers which permit one region of the micro-pattern coating layer 422 to move away from an adjacent region of the micro-pattern coating layer 422 as the stent 410 expands from a collapsed, pre-deployment configuration to an expanded, deployed configuration. In other words, the preferential separation regions 426 may define regions along the stent 410 in which a first portion of the micro-pattern coating layer 422 is designed to separate and space itself away from a second portion of the micro-pattern coating layer 422, with the preferential separation region 426 positioned between the separated first and second portions of the micro-pattern coating 422. It can be appreciated that the preferential separation regions 426 shown in FIG. 9 are positioned in a closed configuration, as the stent 410 has not yet expanded from a collapsed configuration to the expanded configuration.

Figure 9A:
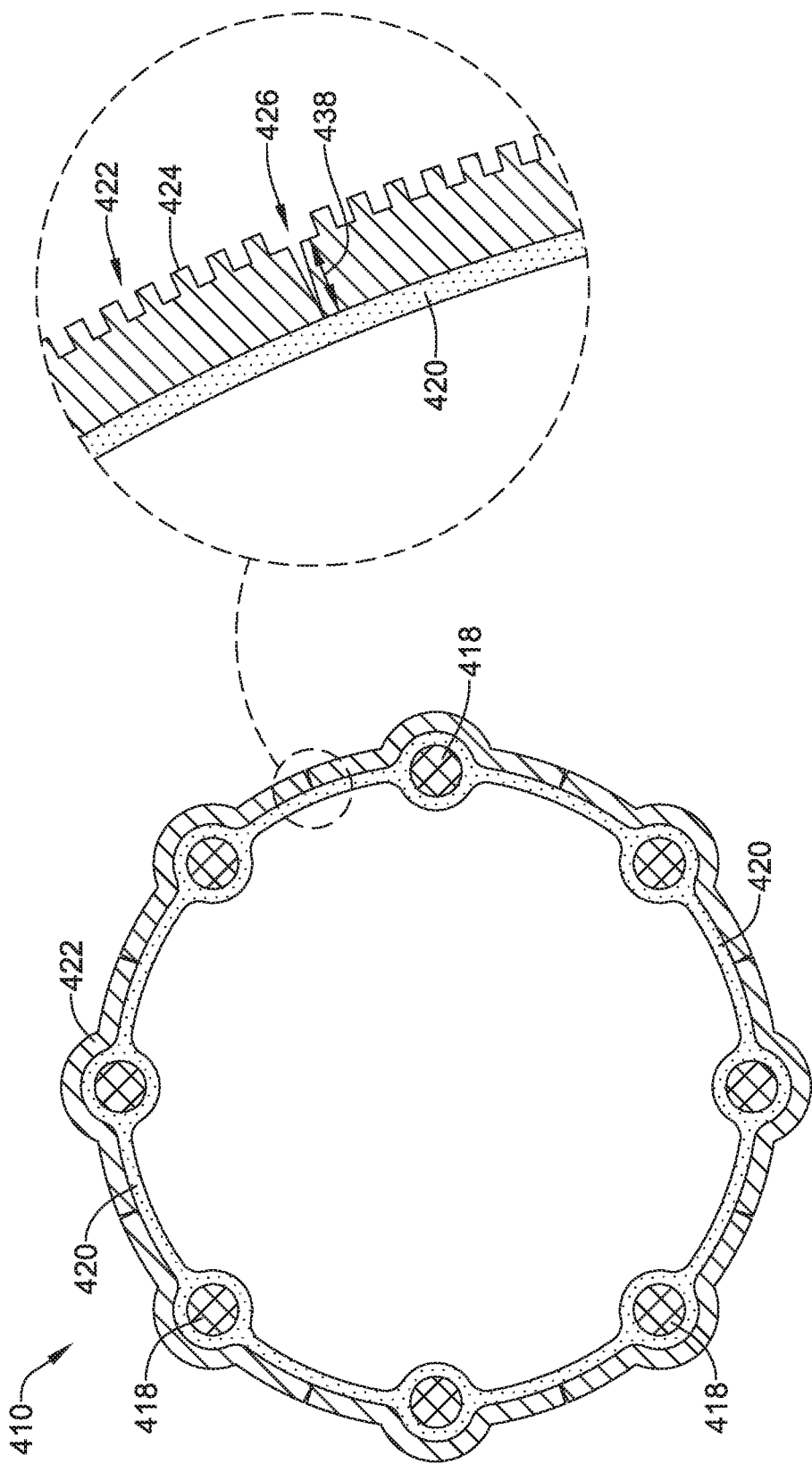
FIG. 9A illustrates a cross-sectional view along line 9A-9A of the stent shown in FIG. 9.

FIG. 9A illustrates a cross-sectional view taken along line 9A-9A of FIG. 9. FIG. 9A shows the base coating layer 420 surrounding each of the individual filaments 418. Additionally, FIG. 9A illustrates that the base coating layer 420 may span across the cell openings of the stent 410. Further, FIG. 9A illustrates the micro-pattern coating layer 422 disposed on the base coating layer 420 (e.g., the micro-pattern coating layer 422 may be applied to an outer surface of the base coating 420). Further yet, the micro-pattern coating layer 422 may extend around the entire circumference of the stent 410 in a radially contracted configuration.

Additionally, the detailed view of FIG. 9A illustrates the micro-pattern coating layer 422 (including the individual anti-migration elements 424) disposed along the base coating layer 420. Further, FIG. 9A shows the preferential separation region 426 extending within the wall 438 of the micro-pattern coating layer 422 (e.g., extending radially inward from an outer surface of the micro-pattern coating layer 422). As shown in FIG. 9A, the preferential separation region 426 may extend only partially through the wall 438 of the coating, such as through of the micro-pattern coating layer 422 to the outer surface of the base coating layer 420. However, it is also contemplated that, in some examples, the preferential separation region 426 may only extend through a portion of the thickness of the micro-pattern coating layer 422, or the preferential separation region 426 may extend into or through the base coating layer 420.

Figure 10:
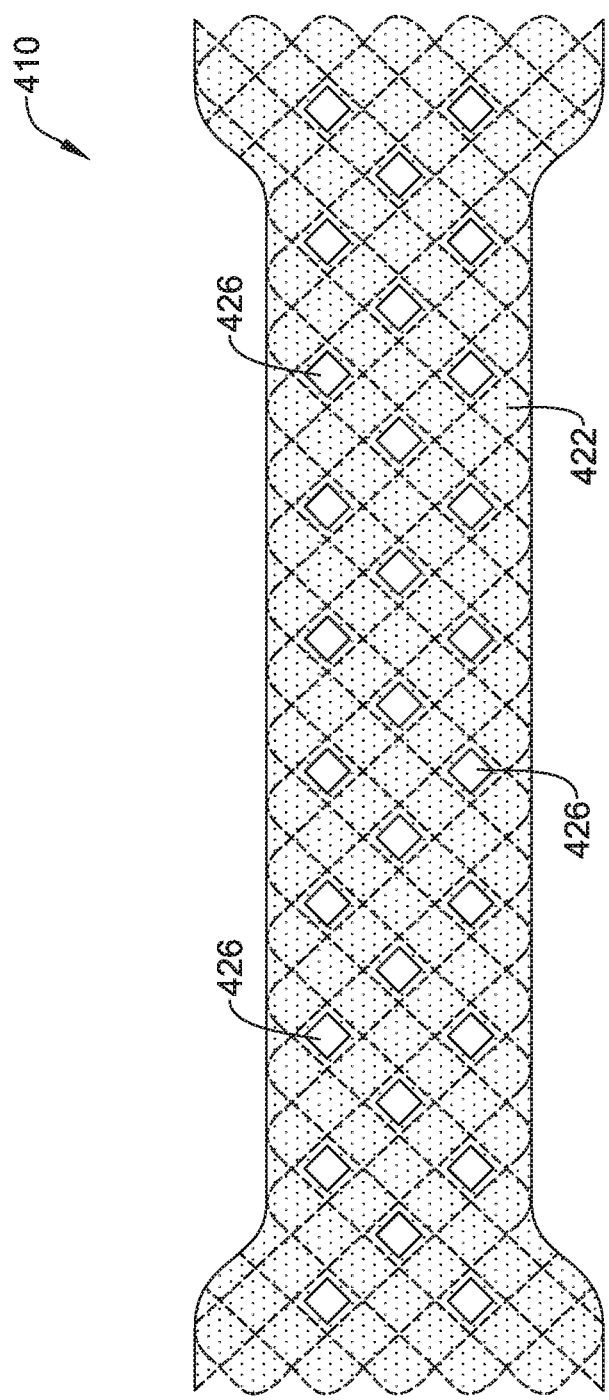
FIG. 10 illustrates the example stent shown in FIG. 9 in a deployed configuration.

FIG. 10 illustrates the stent 410 after having been expanded from the collapsed configuration (shown in FIG. 9) to an expanded configuration. It can be appreciated that as the stent 410 expands, the micro-pattern coating layer 422 may be placed under stress due to expansion forces imparted to the micro-pattern coating layer 422. For example, portions of the micro-pattern coating layer 422 may stretch, and therefore, may be placed under tension. As illustrated in FIG. 10, the opening (e.g., separating) of one or more of the preferential separation regions 426 may mitigate (e.g., relieve) the stress, thereby preventing the micro-pattern coating layer 422 from tearing in undesirable locations, but rather permit predetermined portions of the micro-pattern coating layer 422 to separate from one another. For example, allowing the preferential separation regions 426 to separate adjacent portions of the micro-pattern coating layer 422 (e.g., have one portion of the micro-pattern coating layer 422 separate from another portion of the micro-pattern coating layer 422) may allow the stent 410 to more readily radially expand in a body lumen.

Figure 11:
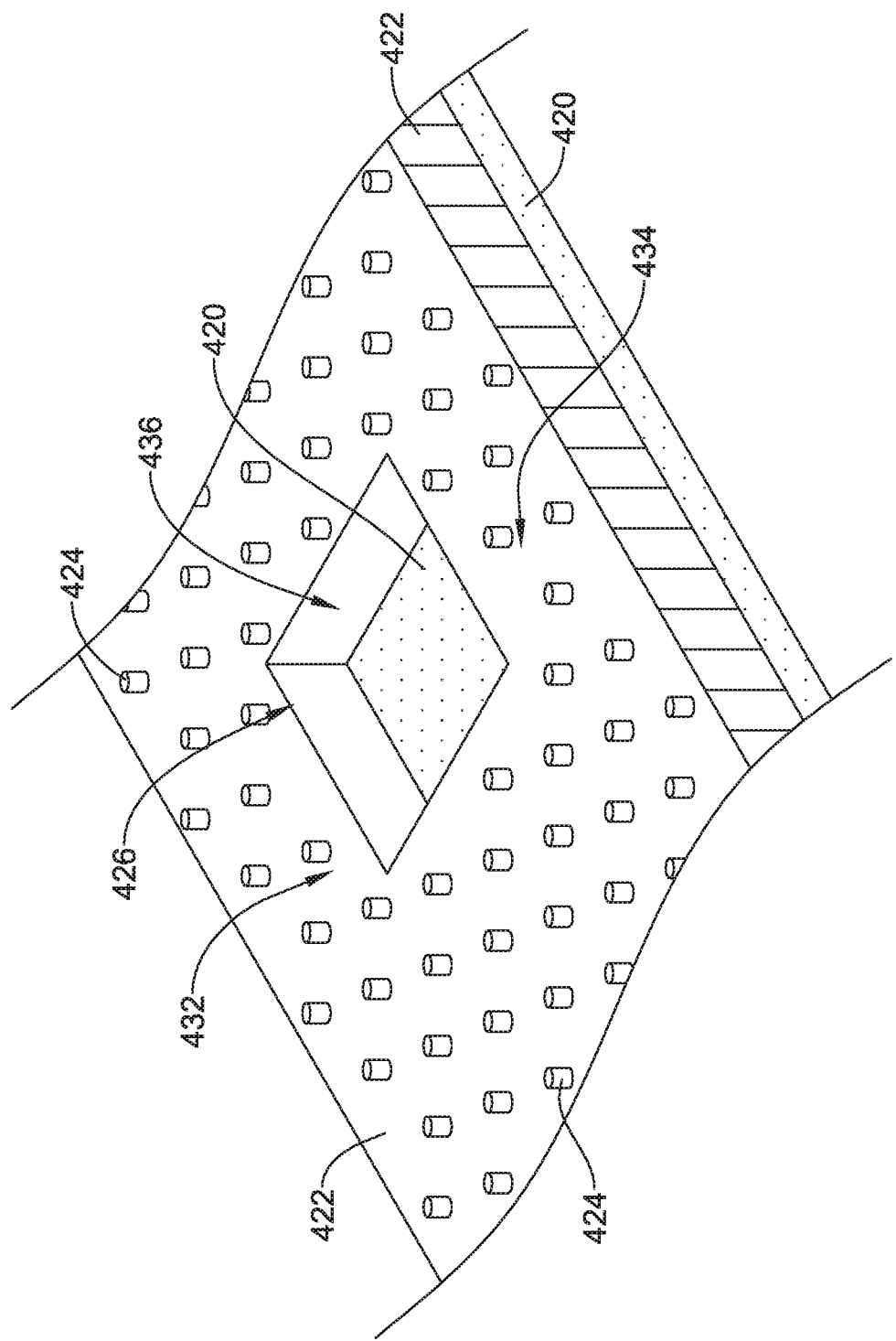
FIG. 11 illustrates a portion of the example stent shown in FIG. 10.

FIG. 11 illustrates a perspective view of one of the example preferential separation regions 426 shown in FIG. 10. It should be noted that, for simplicity, FIG. 11 does not illustrate the stent filaments 418 which may be positioned adjacent to the separation region 426. However, it can be appreciated that while the above discussion illustrates the separation regions 426 as being positioned in the stent cell openings (e.g., the space between the stent filaments 418), it is contemplated that the separation regions 426 may be positioned along any portion of the stent, including along the stent filaments 418.

FIG. 11 shows a preferential separation region 426 in an expanded configuration, whereby a first portion 432 of the micro-pattern coating layer 422 (disposed along the base coating 420 and including the individual anti-migration elements 424) has separated from a second portion 434 of the micro-pattern coating layer 422, with the preferential separation region 426 therebetween. The separation of the first portion 432 from the second portion 434 may create a void (e.g., opening, aperture, hole, etc.) 436 which extends entirely through the wall 438 of the micro-pattern coating layer 422. However, it is also contemplated that, in some examples, the void 436 may only extend through a portion of the wall 438 of the micro-pattern coating layer 422. As shown in FIG. 11, the base coating layer 420 may extend across the void 436 in the radially expanded configuration, thus separating the void 436 from the lumen of the stent 410. The base coating layer 420 may be formed of a material having a greater elasticity than the material of the micro-pattern coating layer 422, such that the base coating layer 420 more readily stretches than the micro-pattern coating layer 422 as the first portion 434 separates from the second portion 434.

In some instances, the shape of the void 436 may differ from the diamond shape shown in FIGS. 10 and 11. For example, the shape of the void 436 may be circular, rectangular, ovular, triangular, polygonal, any suitable geometric shape or combinations thereof. Further, in some instances, the separation regions 426 may be aligned such that they create a perforation. In other words, the size, shape and arrangement of the separation regions 426 may result in a perforation, whereby the coating 420 may tear along the perforation (e.g., the sequential tearing of one void into another) as the stent 410 expands.

Figure 11A:
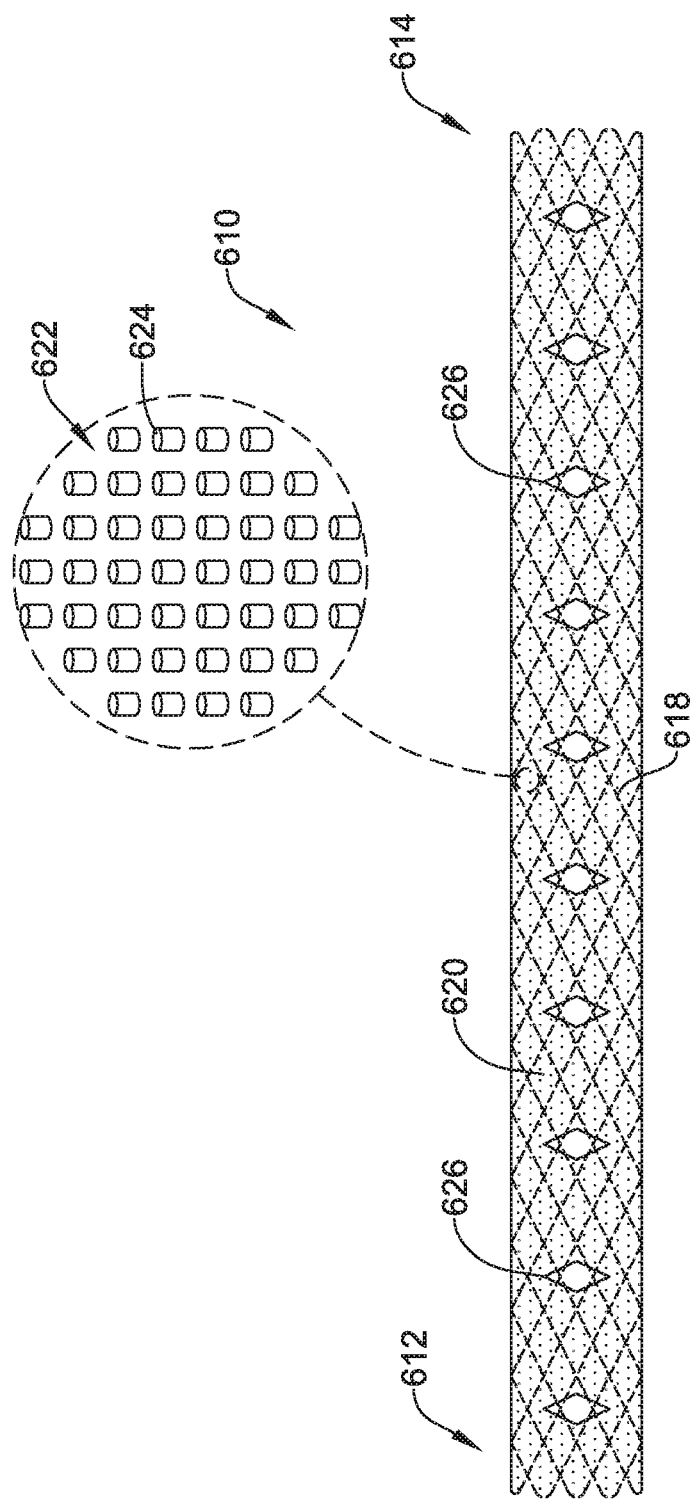
FIG. 11A illustrates another example stent in a pre-deployed configuration having a covered region and a micro-pattern.

FIG. 11A illustrates another example stent 610. The stent 610 may be similar in form and function to other example stents described above. For example, the stent 610 may include an expandable scaffold (including one or more interwoven filaments 618 arranged to form the expandable scaffold) extending from a first end region 612 to a second end region 614. Further, the stent 610 may include a base coating layer 620 disposed along the expandable scaffold of the stent 610. Further yet, the stent 610 may include a micro-pattern coating layer 622 disposed along the base coating layer 620. In some instances, the base coating layer 620 may extend along the entire length and around the entire circumference of the stent 610. The micro-pattern coating layer 622 may be similar in form and function to other micro-pattern coating layers disclosed herein. For example, as shown in the detailed view of FIG. 11A, the micro-pattern coating layer 622 may include a plurality of anti-migration elements 624 extending radially outward from a base portion of the micro-pattern coating layer 622. The anti-migration elements 624 may be designed to provide an additional gripping force to the exterior surface of the stent 610.

Additionally, FIG. 11A illustrates the stent 610 in an unexpanded (e.g., radially contracted, radially constrained, pre-deployed) configuration. In other words, the stent 610 shown in FIG. 11A has a reduced outer diameter as compared to the stent 610 in a deployed, radially expanded configuration (shown in FIG. 11C). In the radially contracted configuration, the stent 610 has an elongated axial length compared to the axial length of the stent 610 in a radially expanded configuration.

Further, in some instances it may be desirable to design the stent 610 to include one or more "preferential separation regions" 626. In the stent example shown in FIG. 11A, the individually-spaced apart separation regions 626 may be spaced longitudinally along the stent 610. For example, the micro-pattern coating layer 622 may include a plurality of discontinuous preferential separation regions 626 arranged at desired intervals along the length and circumference of the stent 610.

It can be appreciated that the preferential separation regions 626 may include strategically placed apertures, notches, slits, slots, channels, grooves, voids, or stress raisers which permit one region of the micro-pattern coating layer 622 to move relative to an adjacent region of the micro-pattern coating layer 622 as the stent 610 expands from a radially collapsed, pre-deployment configuration to a radially expanded, deployed configuration. It can be appreciated that the preferential separation regions 626 shown in FIG. 11A are positioned in an open configuration (e.g., resembling diamond shapes) with the stent 610 in the radially collapsed and axially elongated configuration, prior to radially expanding to the expanded configuration. In other words, the axial elongation of the stent 610 may cause the preferential separation regions 626 to open, moving portions of the micro-pattern coating layer 622 on either side of the preferential separation regions 626 apart.

Figure 11B:
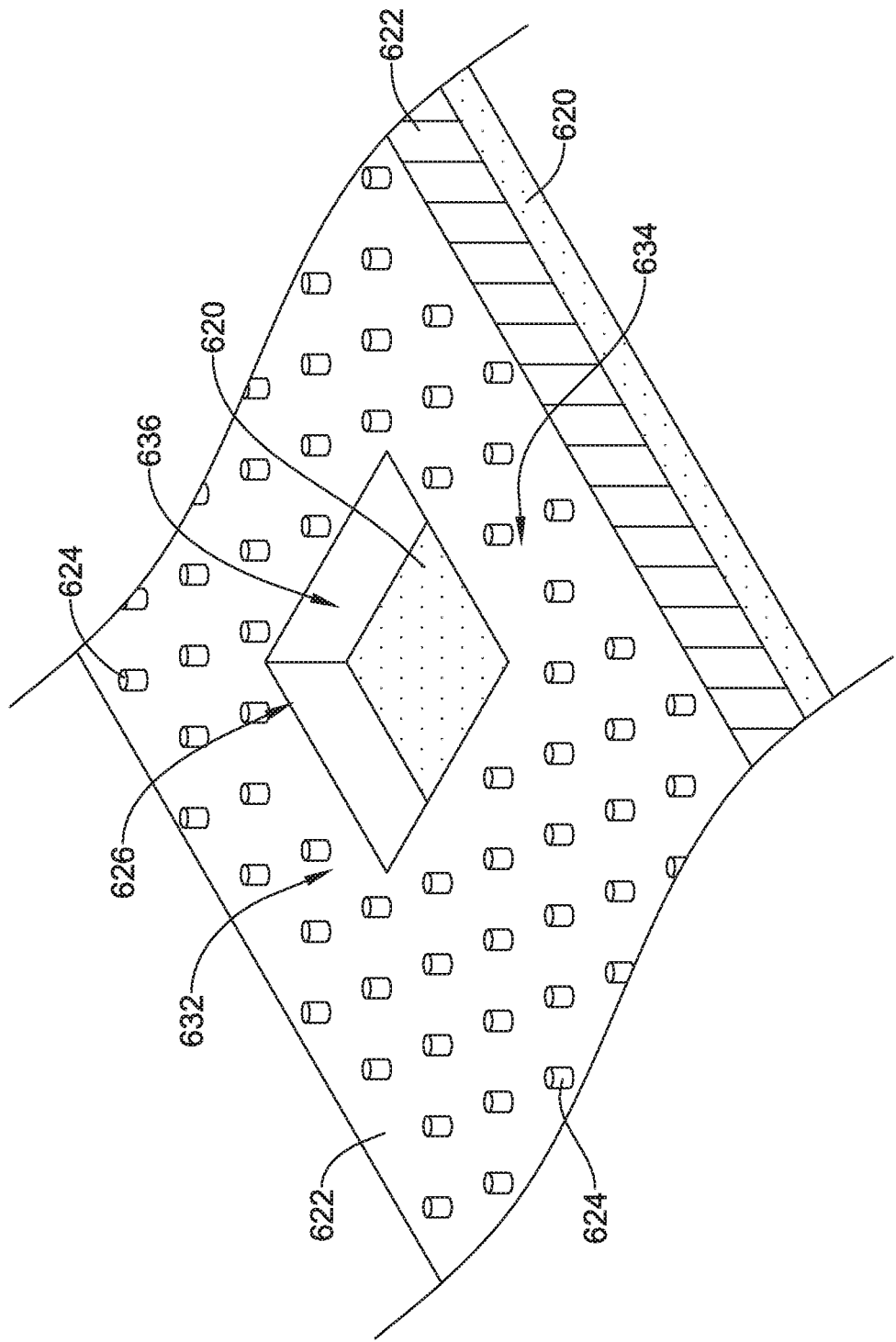
FIG. 11B illustrates a portion of the example stent shown in FIG. 11A.

FIG. 11B illustrates a perspective view of one of the example preferential separation regions 626 shown in FIG. 11A. It should be noted that, for simplicity, FIG. 11B does not illustrate the stent filaments 618 which may be positioned adjacent to the separation region 626. However, it can be appreciated that while the above discussion illustrates the separation regions 626 as being positioned in the stent cell openings (e.g., the space between the stent filaments 618), it is contemplated that the separation regions 626 may be positioned along any portion of the stent 610, including along the stent filaments 618.

FIG. 11B shows a preferential separation region 626 with the stent 610 in the radially collapsed configuration, whereby a first portion 632 of the micro-pattern coating layer 622 (disposed along the base coating 620 and including the individual anti-migration elements 624) is separated from a second portion 634 of the micro-pattern coating layer 622, with the preferential separation region 626 therebetween. The separation of the first portion 632 from the second portion 634 may create a void (e.g., opening, aperture, hole, etc.) 636 which extends entirely through the wall of the micro-pattern coating layer 622. However, it is also contemplated that, in some examples, the void 636 may only extend through a portion of the wall of the micro-pattern coating layer 622. As shown in FIG. 11B, the base coating layer 620 may extend across the void 636 in the radially collapsed configuration, thus separating the void 636 from the lumen of the stent 610. The base coating layer 620 may be formed of a material having a greater elasticity than the material of the micro-pattern coating layer 622, such that the base coating layer 620 more readily stretches than the micro-pattern coating layer 622 when the first portion 634 is separated from the second portion 634.

In some instances, the shape of the void 636 may differ from the diamond shape shown in FIG. 11B. For example, the shape of the void 636 may be circular, rectangular, ovular, triangular, polygonal, any suitable geometric shape or combinations thereof.

Figure 11C:
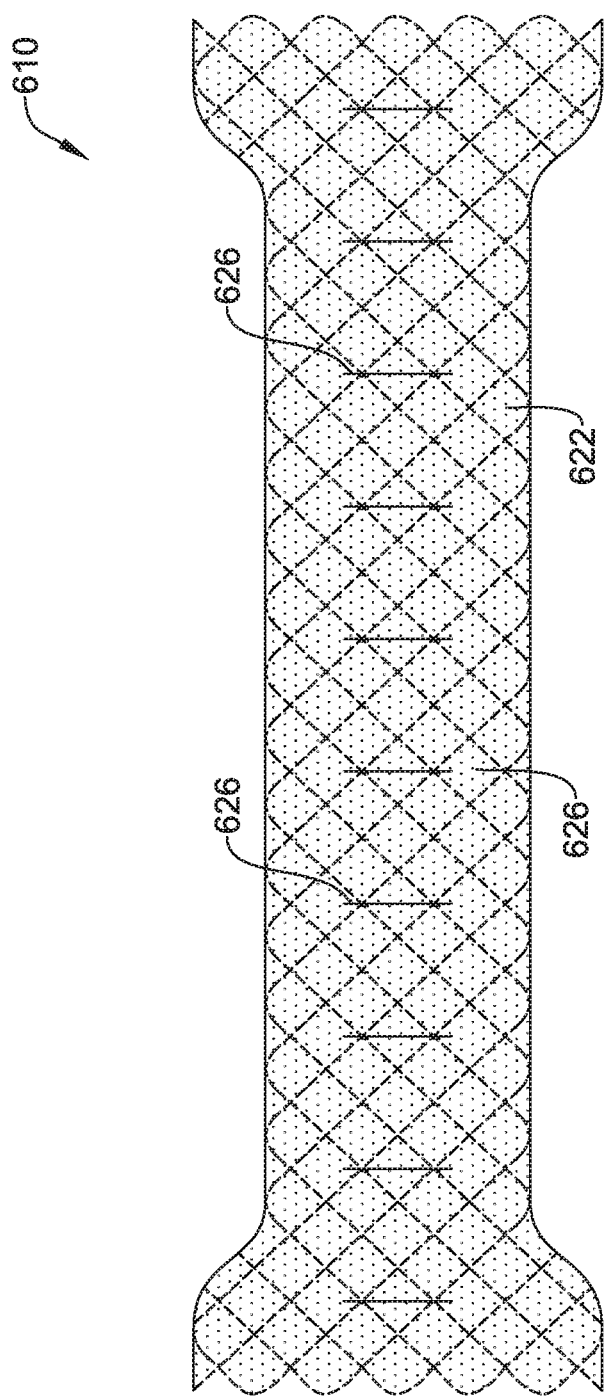
FIG. 11C illustrates the example stent shown in FIG. 11A in a deployed configuration.

FIG. 11C illustrates the stent 610 after having been radially expanded from the radially collapsed configuration (shown in FIG. 11A) to a radially expanded configuration. It can be appreciated from FIG. 11C that as the stent 610 shifts from the collapsed configuration to the expanded configuration, the stent 610 axially contracts and shortens in axial length, which in turn may cause the separation regions 626 to close, moving portions of the micro-pattern coating layer 622 on either side of the preferential separation regions 626 together. This may result in the micro-pattern coating layer 622 to extend substantially continuously across the outer surface of the stent 610. As shown in FIG. 11C, when in the closed configuration, the preferential separation regions 626 may be aligned perpendicular to the longitudinal axis of the stent 610 and extend in a circumferential direction. Thus, the circumferentially opposite ends of the preferential separation regions 626 may move apart when the stent 610 transitions from the radially collapsed, axially elongated configuration to the radially expanded, axially contracted configuration and/or the axially opposite ends of the preferential separation regions 626 may move together when the stent 610 transitions from the radially collapsed, axially elongated configuration to the radially expanded, axially contracted configuration. Accordingly, the circumferentially opposite ends of the preferential separation regions 626 may move together when the stent 610 transitions from the radially expanded, axially contracted configuration to the radially collapsed, axially elongated configuration and/or the axially opposite ends of the preferential separation regions 626 may move apart when the stent 610 transitions from the radially expanded, axially contracted configuration to the radially collapsed, axially elongated configuration.

Figure 12:
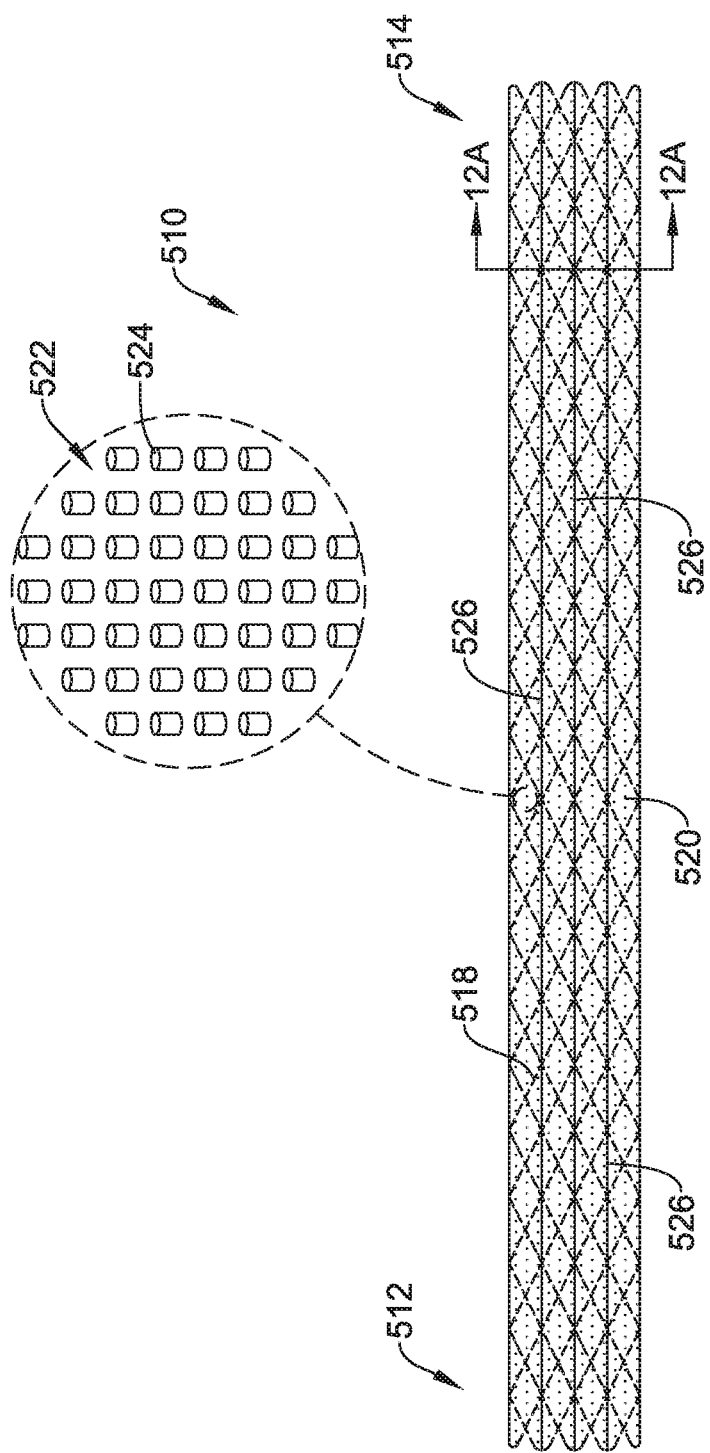
FIG. 12 illustrates another example stent in pre-deployed configuration having a covered region and a micro-pattern.

FIG. 12 illustrates another example stent 510. The stent 510 may be similar in form and function to other example stents described above. For example, the stent 510 may include an expandable scaffold (including one or more interwoven filaments 518 arranged to form the expandable scaffold) extending from a first end region 512 to a second end region 514. Further, the stent 510 may include a base coating 520 disposed along the expandable scaffold of the stent 510. Further yet, the stent 510 may include a micro-pattern coating layer 522 disposed along the base coating layer, whereby the micro-pattern coating layer 522 extends along the entire length and around the entire circumference of the stent 510. The micro-pattern coating layer 522 may be similar in form and function to other micro-pattern coating layers disclosed herein. For example, as shown in the detailed view of FIG. 12, the micro-pattern coating layer 522 may include a plurality of anti-migration elements 524 extending radially outward from a base portion of the micro-pattern coating layer 522. The anti-migration elements 524 may be designed to provide an additional gripping force to the exterior surface of the stent 510.

Additionally, FIG. 12 illustrates the stent 510 in an unexpanded (e.g., pre-deployed) configuration. In other words, the stent 510 shown in FIG. 12 has a reduced outer diameter as compared to the stent 510 in a deployed configuration (shown in FIG. 13). Further, similarly to that described above, in some instances it may be desirable to design the stent 510 to include one or more preferential separation regions 526. However, in the stent example shown in FIG. 12, the separation regions 526 may include longer, continuous, linear "strips" which extend along the longitudinal axis of the stent 510. In some instances, each preferential separation region 526 extends an entire length of the micro-pattern coating layer 522, which in some instances, may be along an entire length of the stent 510.

For example, it can be appreciated that the preferential separation regions 526 may include one or more strategically placed linear slits, channels, grooves, or stress raisers which permit one region of the micro-pattern coating layer 522 to move away from an adjacent region of the micro-pattern coating layer 522 as the stent 510 expands from a collapsed, pre-deployment configuration to an expanded, deployed configuration. In other words, the preferential separation regions 526 may define regions along the stent 510 in which a first portion of the micro-pattern coating layer 522 is designed to separate and space itself away from a second portion of the micro-pattern coating layer 522 with the preferential separation region 526 positioned between the separated first and second portions of the micro-pattern coating 522. It can be appreciated that the preferential separation regions 526 shown in FIG. 12 are positioned in a closed configuration, as the stent 510 has not yet expanded from a collapsed configuration to the expanded configuration.

Figure 12A:
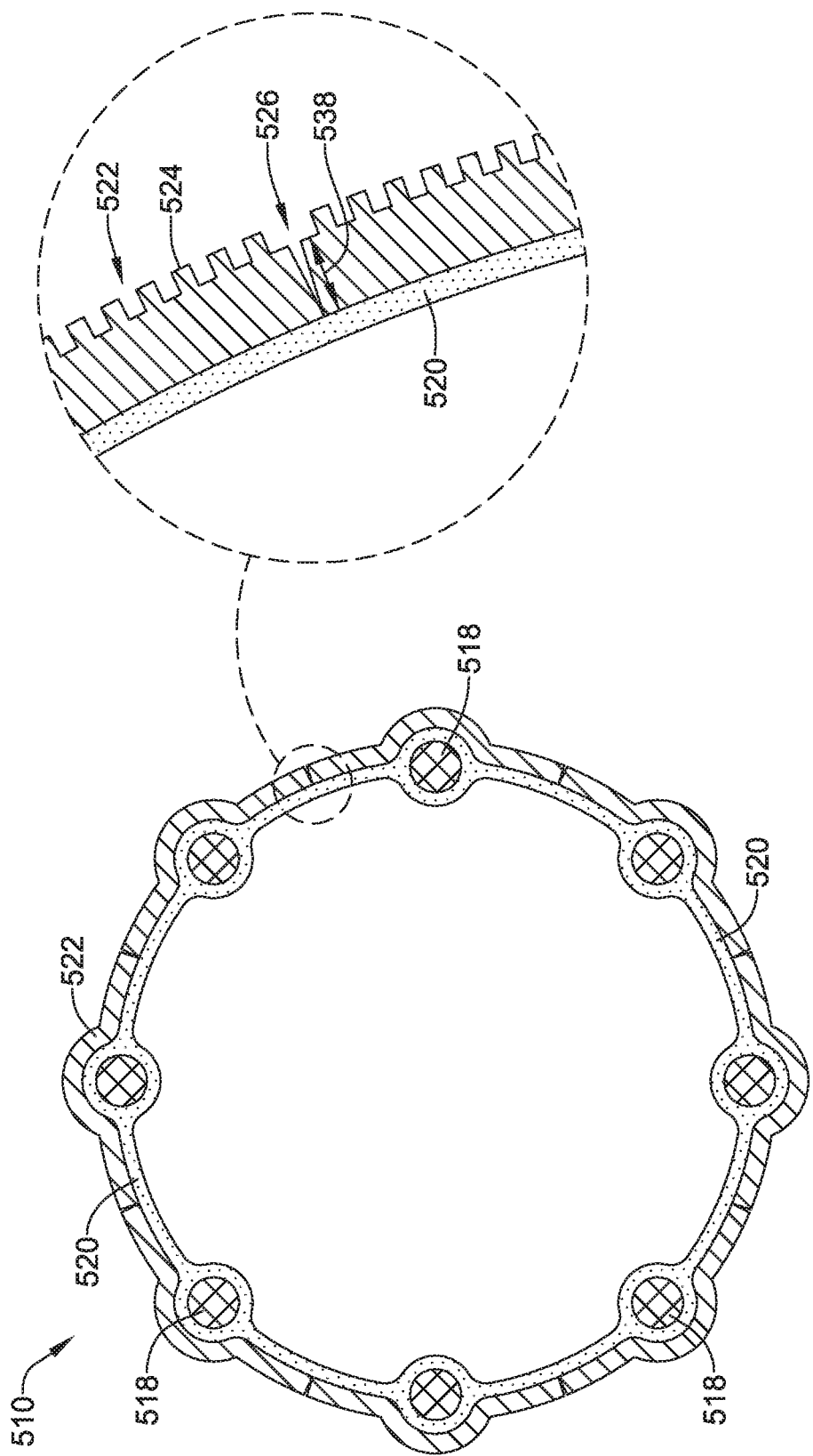
FIG. 12A illustrates a cross-sectional view along line 12A-12A of the stent shown in FIG. 12.

FIG. 12A illustrates a cross-sectional view taken along line 12A-12A of FIG. 12. FIG. 12A shows the base coating layer 520 surrounding each of the individual filaments 518. Additionally, FIG. 12A illustrates that the base coating layer 520 may span across the cell openings of the stent 510. Further, FIG. 12A illustrates the micro-pattern coating layer 522 disposed on the base coating layer 520 (e.g., the micro-pattern coating layer 522 may be applied to an outer surface of the base coating layer 520). Further yet, the micro-pattern coating layer 522 may extend around the entire circumference of the stent 510 in a radially contracted configuration.

Additionally, the detailed view of FIG. 12A illustrates the micro-pattern coating layer 522 (including the individual anti-migration elements 524) disposed along the base coating layer 520. Further, FIG. 12A shows the preferential separation region 526 extending within the wall 538 of the micro-pattern coating layer 522 (e.g., extending radially inward from an outer surface of the micro-pattern coating layer 522). As shown in FIG. 12A, the preferential separation region 526 may extend only partially through the wall 538 of the coating, such as through the micro-pattern coating layer 522 to the outer surface of the base coating layer 520. However, it is also contemplated that, in some examples, the preferential separation region 526 may only extend through a portion of the thickness of the micro-pattern coating layer 522, or the preferential separation region 526 may extend into or through the base coating layer 520.

Figure 13:
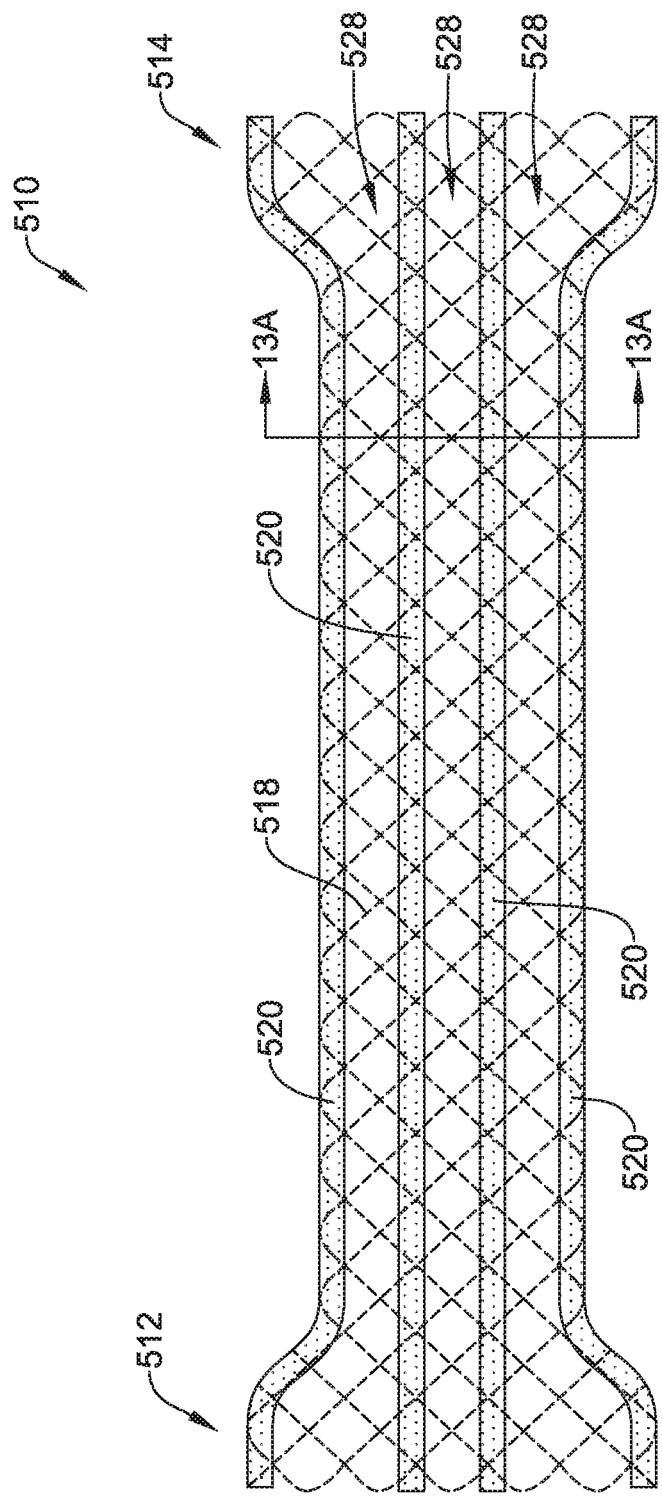
FIG. 13 illustrates the example stent shown in FIG. 12 in a deployed configuration.

FIG. 13 illustrates the stent 510 after having been expanded from the collapsed configuration (shown in FIG.

12) to an expanded configuration. As described above, it can be appreciated that as the stent 510 expands, the micro-pattern coating layer 522 may be placed under stress due to expansion forces imparted to the micro-pattern coating layer 522. Therefore, similarly to the methodology described above with respect to FIGS. 9-11, adjacent portions of the micro-pattern coating layer 522 may separate along the preferential separation regions 526, thereby creating longitudinal channels 528 along the stent surface in which a portion of the base coating layer 520 is exposed between longitudinal strips of the micro-pattern coating layer 522 that have separated from one another.

As illustrated in FIG. 13 (and as described above), the opening (e.g., separating) of one or more of the preferential separation regions 526 may mitigate (e.g., relieve) the stress imparted by the stent deployment forces, thereby preventing the micro-pattern coating layer 522 from tearing in undesirable locations but rather permit predetermined portions of the micro-pattern coating layer 422 to separate from one another. For example, allowing the preferential separation regions 526 to separate adjacent portions of the micro-pattern coating layer 522 (e.g., have one portion of the micro-pattern coating layer 522 separate from another portion of the micro-pattern coating layer 522) may allow the stent 410 to more readily radially expand in a body lumen.

Figure 13A:
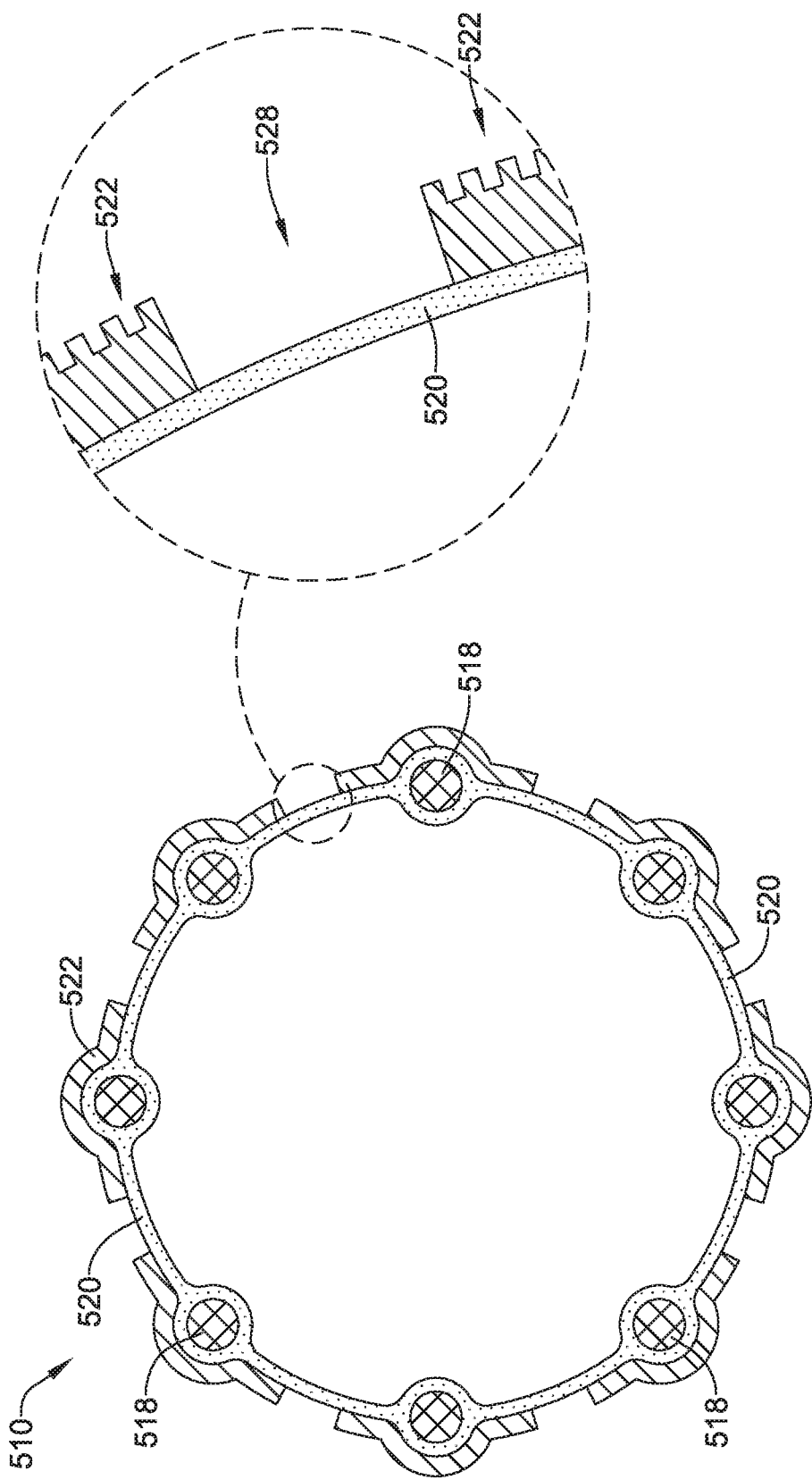
FIG. 13A illustrates a cross-sectional view along line 13A-13A of the stent shown in FIG. 13.

FIG. 13A illustrates a cross-sectional view taken along line 13A-13A of FIG. 13. As described above, FIG. 13A shows the stent 510 in an expanded configuration. FIG. 13A shows the base coating layer 520 surrounding each of the individual filaments 518. Additionally, FIG. 13A illustrates that the base coating layer 520 may span across the cell openings of the stent 510. Further, FIG. 13A illustrates the micro-pattern coating layer 522 disposed on the base coating 520 (e.g., the micro-pattern coating layer 522 may be applied to an outer surface of the base coating 520).

Additionally, the detailed view of FIG. 13A illustrates the micro-pattern coating layer 522 (including the individual anti-migration elements 524) disposed along the base coating 520. Further, FIG. 13A shows the micro-pattern coating layer 522 having expanded along the preferential separation regions 526, whereby the preferential separation regions 526 form expanded "channels" 528 exposing the base coating layer 520 between separated portions (e.g., longitudinal strips) of the micro-pattern coating layer 522 that have been move apart or separated from one another. In other words, as the micro-pattern coating layer 522 expands, one portion of the micro-pattern coating layer 522 separates from an adjacent portion of the micro-pattern coating layer 522 to create the channels 528 along the preferential separation regions 526. As shown in FIG. 13A, the base coating layer 420 may extend across the channels 528 in the radially expanded configuration, thus separating the channels 528 from the lumen of the stent 510. The base coating layer 520 may be formed of a material having a greater elasticity than the material of the micro-pattern coating layer 522, such that the base coating layer 520 more readily stretches than the micro-pattern coating layer 522 as a first longitudinal strip of the micro-pattern coating layer 522 separates from a second longitudinal strip of the micro-pattern coating layer 522.

While FIGS. 12-13A describe the preferential separation regions 526 as linear, longitudinal strips which extend along the entire length (or a portion of the entire length) of the stent 510, it can be appreciated that the preferential separation regions 526 may include other arrangements along the stent 510. For example, the separation regions 526 may extend along the stent 510 in a helical arrangement.

As discussed above, it can be appreciated that any of the micro-pattern coating layers described herein may be configured to prevent the stents described herein from shifting longitudinally or migrating relative to1 an inner surface of a body lumen when the stent is positioned adjacent a target site (e.g., when placed adjacent in the esophagus or intestine). In some instances, the micro-pattern coating layer may include a variety of different textures based upon the specific design and/or size of the anti-migration elements. For example, the surface texture may include points, spikes, spurs, ribs, bumps, ridges, protuberances, etc. which may be configured to project alongside, partially into and/or through the wall of a body lumen, or otherwise engage the wall of a body lumen, thereby providing some degree of interaction (e.g., surface friction, mechanical interlock, interface, engagement, etc.) between the micro-pattern coating layer and the tissue of the body lumen (e.g., esophagus or intestine). The engagement of the textured surface of the micro-pattern coating layer with the tissue of the body lumen may initially prevent the stent from longitudinally shifting or migrating with respect to the body lumen upon implantation within the body lumen. The micro-pattern coating layer composition (including a surface texture) may create friction and/or adhesion with the tissue of the body lumen (e.g., the inner surface of the esophagus or intestine), which may prevent the stent from longitudinally shifting or migrating with respect to the body lumen. For example, in some instances surface texture may be designed to "grip" the inner surface of a body lumen.

The materials that can be used for the various components of any of the stents disclosed herein may include those commonly associated with medical devices. However, this is not intended to limit the materials to those described herein. Rather, the materials that can be used for the various components of any stents disclosed herein may include a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b- styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTEL-LOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, various components of the stents described herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the various components of the stents described herein in determining its location. Some examples of radiopaque materials can include, but are not limited to, gold, platinum, palladium, tantalum, tungsten alloy, polymer material loaded with radiopaque filler, and the like. Additionally, other radiopaque marker bands and/or coils may also be incorporated into the design of the various components of the stents described herein to achieve the same result.

In some embodiments, a degree of Magnetic Resonance Imaging (MRI) compatibility is imparted into the various components of the stents described herein. For example, the various components of the stents described may be made of a material that does not substantially distort the image and create substantial artifacts (e.g., gaps in the image). Certain ferromagnetic materials, for example, may not be suitable because they may create artifacts in an MRI image. The various components of the stents described herein, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical stent for treating a body lumen, comprising:
   an expandable scaffold including a first end region, a second end region opposite the first end region and an outer surface, wherein the expandable scaffold is configured to shift from a radially collapsed state to a radially expanded state; and
   a coating disposed along the outer surface of the expandable scaffold, wherein at least a portion of the coating includes a plurality of anti-migration elements, and wherein the coating further includes a separation region, the separation region positioned between a first region of the coating and a second region of the coating;
   wherein the separation region is configured to permit the first region of the coating to separate from the second region of the coating along the separation region therebetween as the expandable scaffold shifts from the radially collapsed state to the radially expanded state, wherein the separation of the first region of the coating from the second region of the coating creates a plurality of apertures in the coating along the separation region, wherein the plurality of apertures shift between a closed configuration when the expandable scaffold is in the radially collapsed state to an open configuration when the expandable scaffold is in the radially expanded state;
   wherein the coating comprises a base coating disposed along the expandable scaffold and a micro-pattern coating layer disposed over the base coating, the micro-pattern coating layer being formed from the plurality of anti-migration elements and including a wall, the separation region extending within the wall of the micro-pattern coating layer, wherein at least some of the plurality of apertures in the separation region do not extend through the base coating.

2. The medical stent of claim 1, wherein the separation region is configured to prevent the coating from separating from the outer surface of the expandable scaffold when the expandable scaffold shifts from the radially collapsed state to the radially expanded state.

3. The medical stent of claim 1, wherein at least some of the plurality of apertures extend entirely through the wall of the micro-pattern coating layer and the base coating.

4. The medical stent of claim 1, wherein the wall of the micro-pattern coating layer has a radial thickness defined between an outermost surface of the wall and an outer surface of the base coating, wherein at least some of the plurality of apertures extend only partially through the radial thickness of the wall of the micro-pattern coating layer.

5. The medical stent of claim 1, wherein the plurality of apertures are aligned along a longitudinal axis of the stent.

6. The medical stent of claim 5, wherein the alignment of the plurality of apertures of the separation regions create a perforated separation region.

7. The medical stent of claim 1, wherein the separation region extends continuously along a longitudinal axis of the stent from the first end region to the second end region.

8. The medical stent of claim 7, wherein the separation region extends linearly along the longitudinal axis of the stent.

9. The medical stent of claim 7, wherein the preferential separation region extends non-linearly along the longitudinal axis of the stent.

10. The medical stent of claim 1, wherein the expandable scaffold includes a plurality of interwoven filaments, and wherein the plurality of filaments are arranged to define a plurality of cells therebetween, and wherein the separation region is positioned within one of the plurality of cells.

11. A medical stent for treating a body lumen, comprising:
an expandable scaffold including a first end region, a second end region opposite the first end region and an outer surface, wherein the expandable scaffold is configured to shift from a radially collapsed state to a radially expanded state; and
a coating disposed along the outer surface of the expandable scaffold, wherein at least a portion of the coating includes a plurality of anti-migration elements disposed thereon;
wherein the coating further includes a plurality of separation regions, each of the separation regions spaced apart from one another, and wherein each of the separation regions is configured to define an aperture in the coating that shifts from a closed configuration to an open configuration when the expandable scaffold shifts from the radially collapsed state to the radially expanded state;
wherein the coating comprises a base coating disposed along the expandable scaffold and a micro-pattern coating layer disposed over the base coating, the micro-pattern coating layer being formed from the plurality of anti-migration elements and including a wall, the separation region extending within the wall of the micro-pattern coating layer, wherein the aperture in at least some of the plurality of separation regions does not extend through the base coating.

12. The medical stent of claim 11, wherein each of the separation regions is positioned between a first region of the coating and a second region of the coating, and wherein each of the separation regions is configured to permit the first region of the coating to separate from the second region of the coating along each separation region therebetween as the expandable scaffold shifts from the radially collapsed state to the radially expanded state.

13. The medical stent of claim 11, wherein each of the plurality of separation regions is configured to prevent the coating from separating from the outer surface of the expandable scaffold when the expandable scaffold shifts from the radially collapsed state to the radially expanded state.

14. The medical stent of claim 11, wherein the aperture of each of the preferential separation regions extends entirely through the wall of the micro-pattern coating layer.

15. The medical stent of claim 11, wherein the wall of the micro-pattern coating layer has a radial thickness defined between an outermost surface of the wall and an outer surface of the base coating, wherein the aperture of at least some of the separation regions extends only partially through the radial thickness of the wall of the micro-pattern coating layer.

16. The medical stent of claim 11, wherein each of the separation regions extends continuously along a longitudinal axis of the stent from the first end region to the second end region.

17. The medical stent of claim 11, wherein each of the separation regions are spaced apart from one another along a longitudinal axis of the stent.

18. The medical stent of claim 11, wherein the expandable scaffold includes a plurality of interwoven filaments, and wherein the plurality of filaments are arranged to define a plurality of cells therebetween, and wherein each of the separation regions is positioned within a corresponding cell of the plurality of cells.

19. A medical stent, comprising:
an expandable scaffold including a first end region, a second end region opposite the first end region and an outer surface, wherein the expandable scaffold is configured to shift from a radially collapsed state to a radially expanded state, and wherein the expandable scaffold includes a plurality of interwoven filaments defining a plurality of cell openings located therebetween; and
a coating disposed along the outer surface of the expandable scaffold, wherein at least a portion of the coating includes a micro-pattern, the micro-pattern including a plurality of individual spaced-apart anti-migration elements;
wherein the micro-pattern is disposed within the cell openings between the interwoven stent filaments;
wherein the coating comprises a base coating disposed along the expandable scaffold and a micro-pattern coating layer disposed over the base coating, the micro-pattern coating layer being formed from a single monolithic structure including a base layer with the plurality of individual spaced-apart anti-migration elements extending radially therefrom, wherein the base coating and the micro-pattern coating layer are separate layers formed from different materials.

* * * * *